US 7,157,264 B2
Jan. 2, 2007

(12) United States Patent
Shaw

(10) Patent No.: US 7,157,264 B2
(45) Date of Patent: Jan. 2, 2007

(54) MODIFIED TARGET ENZYMES HAVING CATALYTIC TRIADS AND USES THEREOF

(75) Inventor: Andrew Shaw, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 432 days.

(21) Appl. No.: 10/068,374

(22) Filed: Feb. 6, 2002

(65) Prior Publication Data

US 2003/0044903 A1     Mar. 6, 2003

Related U.S. Application Data

(60) Provisional application No. 60/268,347, filed on Feb. 12, 2001.

(51) Int. Cl.
 *C12N 9/42* (2006.01)
 *C12N 1/20* (2006.01)
 *C12N 15/00* (2006.01)

(52) U.S. Cl. ............... 435/209; 435/252.3; 435/320.1; 435/278; 435/325; 536/23.2

(58) Field of Classification Search ............... 435/209, 435/252.3, 320.1, 278, 325; 536/23.2
See application file for complete search history.

(56) References Cited

U.S. PATENT DOCUMENTS 6,063,611 A   5/2000  Van Solingen ............. 435/209

FOREIGN PATENT DOCUMENTS

EP        0 739 982 A1   10/1996

OTHER PUBLICATIONS

Lowe, M. E. Biochimica et Biophysica Acta (Jul. 26, 1996) 1302 (2) : 177-83 (Abstract Only).*
Beguin, P., "Molecular Biology of Cellulose Degradation", *Ann Rev. Microbiol*, 1990 vol. 44, pp. 219-248.
Davies et al., "Structure of the *Bacillus agaradherans* Family 5 Endoglucanase at 1.6 A and Its Celobiose Complex at 2.0 Resolution", *Biochemistry*, 1998, vol. 37, pp. 1926-1932.
DeSantis et al., " Chemical Modifications at a Single Site Can Induce Significant Shifts in the pH Profiles of a Serine Protease", *J. Am. Chem. Soc.*, 1998 vol. 120, pp. 8582-8586.
Dodson et al., "Catalytic triads and their relatives", *TIBS*, 1998, vol. 23(9), pp. 347-352.
Shaw et al., "A Novel Combination of Two Classic Catalytic Schemes", *J. Mol. Biol.*, Jul. 2002, vol. 320, pp. 303-309.
Shirai et al., "Crystal Structure of Alkaline Cellulase K : Insight into the Alkaline Adaptation of an Industrial Enzyme", Jul. 2001, vol. 310, pp. 1079-1087.
Wang et al., "Glu280 Is the Nucleotiphile in the Active Site of Clostridium thermocellum CelC, a Family A Endo-Beth-1, 4-glucanase," *J. Biol. Chem.*, Jul. 5, 1993, V268(19), pp. 14096-14106.
Band et al., "*Bacillus subtilis* Requires a "Stringent" Shine-Dalgarno Region for Gene Expression,", *DNA*, 3:17-21 (1984).

Blake et al., *Nature*, 206:757 (1965).
Blow et al., "Role of a Buried Acid Group in the Mechanism of Action of Chymotrypsin," *Nature*, 221:337-340 (1969).
Brunger, *X-plor Version 3.1 A system for X-ray crystallography and NMR*, Yale University Press, New Haven CT, 1992 Software program.
Courtney et al., "Synthesis in *E. coli* of beta, -antitrypsin variants for therapeutic potential for emphysema and thrombosis," *Nature*, 313:149-157 (1985).
Craik et al., "Redesigning Trypin: Alteration of Substrate Specificity," *Science*, 228:291-297 (1985).
Cutfield et al., "The Structure of the Exo-beta-(1,3)-Glucanase from *Candida albicans* in Native and Bound Forms: Relationship between a Pocket and Groove in Family 5 Glycosyl Hydrolases," *J. Mol. Biol.*, 294:771-783 (1999).
Davies et al., "Snapshots along an Enzymatic Reaction Coordinate: Analysis of a Retaining beta-Glycoside Hydrolase," *Biochemistry*, 37:11707-11713 (1998).
Davies et al., " Structures and mechanisms of glycosyl hydrolases," *Structure*, 3:853 (1995).
Dominguez et al.," The Crystal Structure ofb a Family 5 Endoglucanase Mutant in Complexed and Uncomplexed Forms Reveals an Induced Fit Activation mechanism," *J. Mol. Biol.*, 257:1042-1051 (1996).
Dorrell et al., "Improved Efficiency of Inverse PCR Mutagenesis," *Biotechniques*, 21:604, 606, 608 (1996).
Ducros et al. "Crystal structure of the catalytic domain of a bacterial cellulase belonging to family 5", *Structure*, 3:939-949 (1995).
Estell et al, "Engineering an Enzyme by Site-directed Mutagenesis to be Resistant to Chemical Oxidation," *J Biol Chem* (1985) 260:6518-6521.
Estell et al., "Probing Steric and Hydrophobic Effects on Enzyme-Substrate Interactions by Protein Engineering," *Science*, 233:659-663 (1986).
Ford et al., "Crystal Structure of a Lysozyme—Tetrasaccharide Lactone Complex," *J. Mol. Biol.*, 88:349 (1974).
Hilge et al., "High-resolution native and complex structures of thermostable beta-mannanase from Thermomonospora fusca—substrate specificity in glycosyl hydrolase family 5," *Structure*, 6:1433-1444 (1998).
Holm et al., "Random mutagenesis used to probe the structure and function of *Bacillus stearothermophilus* alpha-amylase," *Prot. Engineering* (1990) 3:181-191.

(Continued)

Primary Examiner—Tekchand Saidha
(74) *Attorney, Agent, or Firm*—Genencor International, Inc.

(57) ABSTRACT

Modified target molecules are disclosed comprising genetically modified molecules, preferably enzymes, that include a catalytic triad which alters the performance of the polypeptide. Optionally, such a catalytic triad in the modified target molecule comprises three members equivalent to amino acid residues Serine 227, Histidine 200, or Glutamate 139, respectively, in the Bacillus cellulase 103 sequence. Using the embodiments disclosed by the present invention, altered performance profiles, such as enzyme activity or stability, under alkaline conditions can be achieved. Methods of making and using modified target molecules are also disclosed.

6 Claims, 8 Drawing Sheets

OTHER PUBLICATIONS

Hsu et al., "Penicillopepsin from *Penicillum janthinellum* crystal structure at 2.8 Å and sequence homology with porcine pepsin," *Nature*, 266:140-145 (1977).

Janecek et al., "α-Amylases and approaches leading to their enhanced stability," *FEBS* (1992) 304:1-3.

Janecek et al., "Evolution of Parallel β/α Barrel Enzyme Family Lightened by Structural Data on Starch-Processing Enzymes," *J Prot Chem* (1993) 12:509-514.

Jespersen et al., "Starch- and Glycogen-Debranching and Branching Enzymes: Prediction of Structural Features of the Catalytic $(\alpha/\beta)_8$-Barrel Domain and Evolutionary Relationship to Other Amylolytic Enzymes," *J Prot Chem* (1993) 12:791-805.

Johnson et al., "Structure of some crystalline Lysozyme-inhibitor complexes determined by x-ray analysis at 6 Å resolution," *Nature*, 206:761 (1965).

Kelly et al., "X-ray crystallography of the binding of the bacterial cell wall trisaccharide NAM-NAG-NAM to lysozyme," *Nature*. : 28:875 (1979).

Kuhn et al., "The 0.78 A Structure of a Serine protease: *Bacillus lentus* Subtilisin," *Biochemistry*, 37:13446-13452 (1998).

LaFortelle et al., *Methods in Enzymology*, 276:472-493 (1997)—Book Listed but not sent.

Matthews et al.,"Three-dimensional Structure of Tosyl-alpha-chymotrypsin," *Nature*, 214:652-656 (1967).

MacGregor et al., "A super-secondary structure predicted to be common to several alpha-1,4-D-glucan-cleaving enzymes," *Biochem. J.*, 259:145-152 (1989).

Matsui et al., "A mutant α-amylase with enhanced activity specific for short substrates," *FEBS* (1992) 310:216-218.

Matsui et al., "Roles of the Aromatic Residues Conserved in the Active Center of Saccharomycopsis alpha-Amylase for Transglycosylation and Hydrolysis Activity," *Febs Letters*, 310:216-218 (1994).

McGavin et al., "Structure of the cel-3 Gene from *Fibrobacter succinogenes* S85 and Characteristics of the Encoded Gene Product, Endoglucanase 3," *J. Bacteriol.*, 171:5587-5595 (1989).

McIntosh et al., "Theb pKa of the General Acid/Base carboxyl Group of a Glycosidase Cycles during Catalysis : A $^{13}$C-NMR Study of Bacillus circulans Xylanase," *Biochemistry*, 35:9958-9966 (1996).

McRee, "XtalView/Xfit—A Versatile Program for Manipulating Atomic Coordinates and Electron Density," *J. Struct. Biol.*, 125:156-165 (1999).

Miller et al., "Crystal structure of a retroviral protease proves relationship to aspartic protease family," *Nature*, 337:576 (1989).

Naki et al., "Selection of a subtilisin-hyperproducing Bacillus in a highly structured environment," *Applied Microbiology and Biotechnology*, 49:290-294 (1998).

Park et al., "Identification of two amino acids contributing the high enzyme activity in the alkaline pH range of an alkaline endoglucanase from a Bacillus sp.," *Protein Eng.*, 6:921-926 (1993).

Pennisi, "In Industry, Extremophiles Begin to Make Their Mark," *Science*, 276;705 (1997).

Perry et al., Disulfide Bond Engineered in to T4 Lysozyme : Stabilization of the Protein Toward Thermal Inactivation, *Science*, 226:555-557 (1984).

Phillips, "On the stereochemical basis of enzyme action: Lessons from Lysozyme," *Harvey Lectures*, 66:135 (1971).

Rosenburg et al., "Synthesis in yeast of a functional oxidation-resistant mutant of human alpha1-antitrypsin," *Nature*, 312:77-80 (1984).

Sabini et al., "The three-dimensional structure of a *Trichodema reesei* beta-mannanase from glycoside hydrolase family 5," *Acta Crystall, D. Biol. Crystall.*, 56:3-13 (2000).

Sakon et al., "Crystal Structure of Thermostable Family 5 Endocellulase E1 from *Acidothermus cellulolyticus* in Complex with Cellotetraose," *Biochemistry*, 35:10648-10660 (1996).

Schrag et al., "Ser-His-Glu triad forms the catalytic site of the lipase from *Geotrichum candidum*," *Nature*, 351:761-764 (1991).

Sogaard et al., "α-Amylases: Structure and function," *Carbohydrate Polymers* (1993) 21:137-146.

Sogaard et al., "Site-directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α-amylase 1," *J Biol Chem* (1993) 268:22480-22484.

*Starke*, ' 45:232-237 (1993)—Cite Incomplete.

Svensson et al., "Mutational analysis of glycosylase function," *J Biotech* (1993) 29:1-37.

Svensson, "Protein engineering in the α-amylase family: catalytic mechanism, substrate specificity, and stability," *Plant Mol Biol* (1994) 25:141-157.

Takase et al., "Site-directed mutagenesis of active site residues in *Bacillus subtilis* α-amylase," *Biochemica et Biophysica Acta* (1992) 1120:281-288.

Vihinen et al., "Site-Directed Mutagenesis of a Thermostable α-Amylase from *Bacillus stearothermophilus*: Putative Role of Three Conserved Residues," *J Biochem* (1990) 107-:267-272.

Villafranca et al., "Directed Mutagenesis of Dihydrofolate Reductase," *Science*, 222:782-788 (1983).

Wells et al., "Designing substrate specificity by protein engineering of electrostatic interactions," *Proc. Natl. Acad. Sci. USA*, vol. 84, pp. 1219-1223 (Mar. 1987).

White et al., "Mechanism of catalysis by retaining Beta-glycosyl hydrolases," *Curr. Op. Struct. Biol;*, 7:645 (1997).

Yoshigi et al., *J. Biochem. (Tokyo)*, 108:388-392 (1990).

* cited by examiner

A
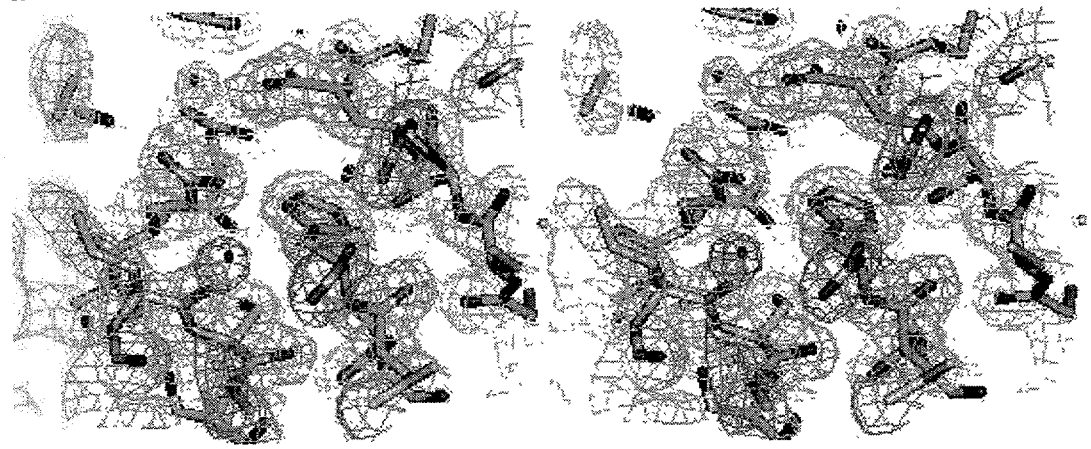
B
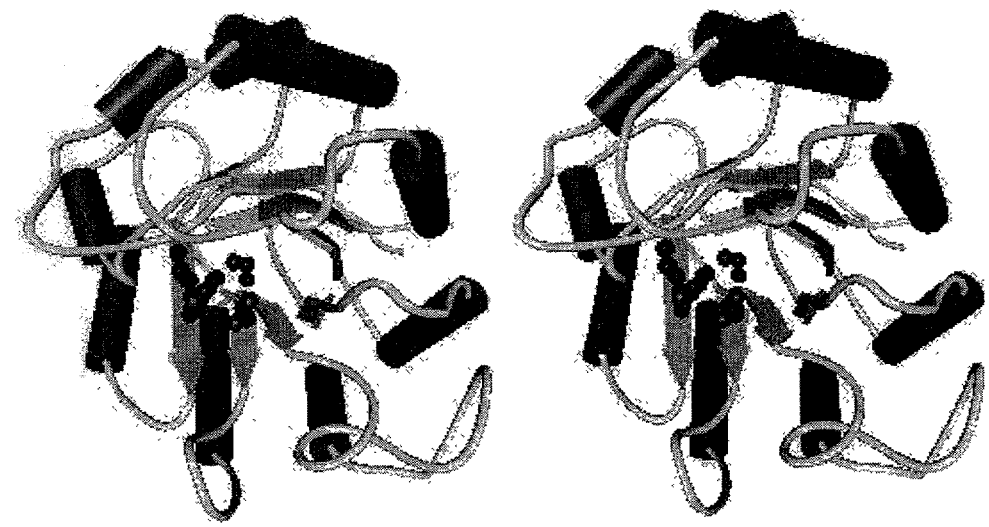
FIGURE 1 A & B

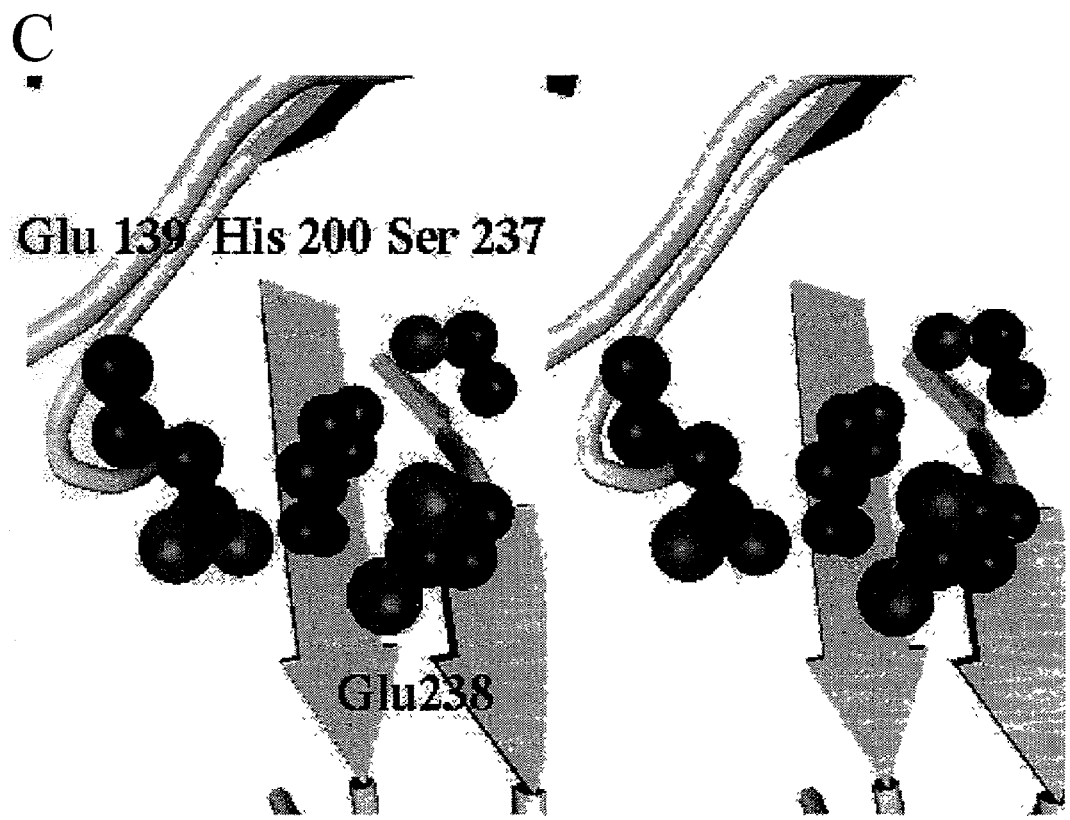
FIGURE 1 C

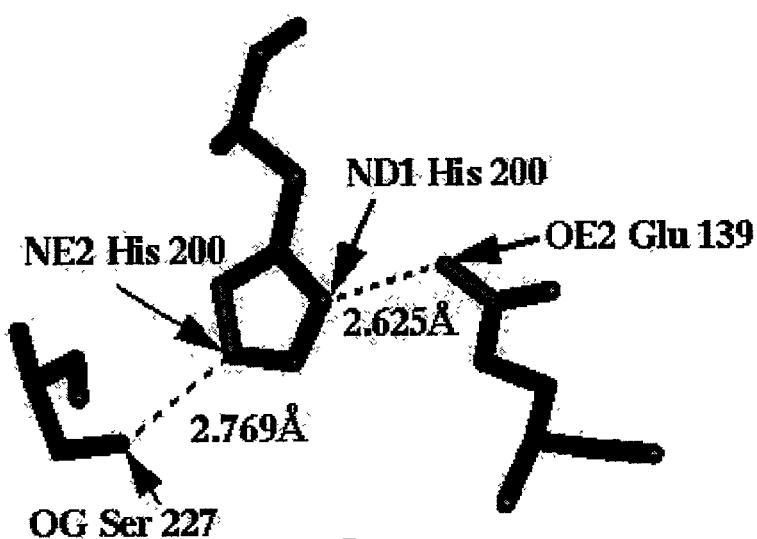
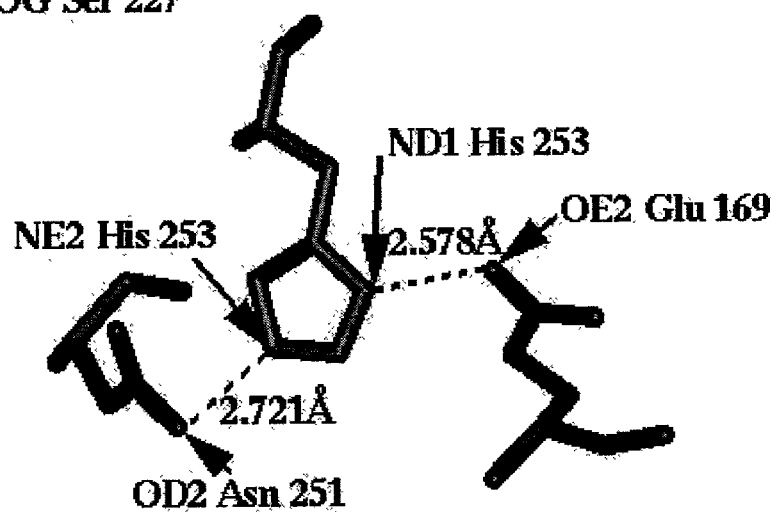
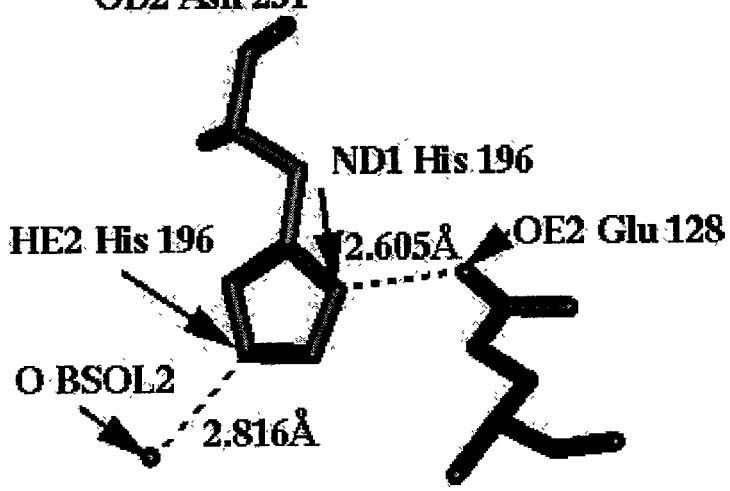
FIGURE 2 A, B & C

FIGURE 3A (2) INFORMATION FOR SEQ ID NO: 1:

(i) SEQUENCE CHARACTERISTICS:
        (A) LENGTH: 1404 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Bacillus sp.
        (C) INDIVIDUAL ISOLATE: CBS 670.93

(ix) FEATURE:
        (A) NAME/KEY: sig_peptide
        (B) LOCATION: 1..78

(ix) FEATURE:
        (A) NAME/KEY: mat_peptide
        (B) LOCATION: 79..1404
        (D) OTHER INFORMATION: /function= "endoglucanase"
            /EC_number= 3.2.1.4
            /product= "BCE103 cellulase"

(ix) FEATURE:
        (A) NAME/KEY: CDS
        (B) LOCATION: 1..1404

(xi) SEQUENCE DESCRIPTION: SEQ ID NO: 1:

```
ATG AAA AAG ATA ACT ACT ATT TTT GCC GTA TTG CTC ATG ACA TTG GCG        48
Met Lys Lys Ile Thr Thr Ile Phe Ala Val Leu Leu Met Thr Leu Ala
-26 -25              -20                  -15
```

FIGURE 3B

```
TTG TTC AGT ATA GGA AAC ACG ACA GCG GCT GAT GAT TAT TCA GTT GTA     96
Leu Phe Ser Ile Gly Asn Thr Thr Ala Ala Asp Asp Tyr Ser Val Val
-10              -5                   1                   5

GAG GAA CAT GGG CAA CTA AGT ATT AGT AAC GGT GAA TTA GTC AAT GAA    144
Glu Glu His Gly Gln Leu Ser Ile Ser Asn Gly Glu Leu Val Asn Glu
            10                  15                  20

CGA GGC GAA CAA GTT CAG TTA AAA GGG ATG AGT TCC CAT GGT TTG CAA    192
Arg Gly Glu Gln Val Gln Leu Lys Gly Met Ser Ser His Gly Leu Gln
        25                  30                  35

TGG TAC GGT CAA TTT GTA AAC TAT GAA AGC ATG AAA TGG CTA AGA GAT    240
Trp Tyr Gly Gln Phe Val Asn Tyr Glu Ser Met Lys Trp Leu Arg Asp
    40                  45                  50

GAT TGG GGA ATA ACT GTA TTC CGA GCA GCA ATG TAT ACC TCT TCA GGA    288
Asp Trp Gly Ile Thr Val Phe Arg Ala Ala Met Tyr Thr Ser Ser Gly
55                  60                  65                  70

GGA TAT ATT GAC GAT CCA TCA GTA AAG GAA AAA GTA AAA GAG ACT GTT    336
Gly Tyr Ile Asp Asp Pro Ser Val Lys Glu Lys Val Lys Glu Thr Val
                75                  80                  85

GAG GCT GCG ATA GAC CTT GGC ATA TAT GTG ATC ATT GAT TGG CAT ATC    384
Glu Ala Ala Ile Asp Leu Gly Ile Tyr Val Ile Ile Asp Trp His Ile
            90                  95                  100

CTT TCA GAC AAT GAC CCG AAT ATA TAT AAA GAA GAA GCG AAG GAT TTC    432
Leu Ser Asp Asn Asp Pro Asn Ile Tyr Lys Glu Glu Ala Lys Asp Phe
        105                 110                 115

TTT GAT GAA ATG TCA GAG TTG TAT GGA GAC TAT CCG AAT GTG ATA TAC    480
Phe Asp Glu Met Ser Glu Leu Tyr Gly Asp Tyr Pro Asn Val Ile Tyr
    120                 125                 130

GAA ATT GCA AAT GAA CCG AAT GGT AGT GAT GTT ACG TGG GAC AAT CAA    528
Glu Ile Ala Asn Glu Pro Asn Gly Ser Asp Val Thr Trp Asp Asn Gln
135                 140                 145                 150

ATA AAA CCG TAT GCA GAA GAA GTG ATT CCG GTT ATT CGT GAC AAT GAC    576
Ile Lys Pro Tyr Ala Glu Glu Val Ile Pro Val Ile Arg Asp Asn Asp
                155                 160                 165

CCT AAT AAC ATT GTT ATT GTA GGT ACA GGT ACA TGG AGT CAG GAT GTC    624
Pro Asn Asn Ile Val Ile Val Gly Thr Gly Thr Trp Ser Gln Asp Val
            170                 175                 180

CAT CAT GCA GCC GAT AAT CAG CTT GCA GAT CCT AAC GTC ATG TAT GCA    672
His His Ala Ala Asp Asn Gln Leu Ala Asp Pro Asn Val Met Tyr Ala
        185                 190                 195

TTT CAT TTT TAT GCA GGA ACA CAT GGA CAA AAT TTA CGA GAC CAA GTA    720
Phe His Phe Tyr Ala Gly Thr His Gly Gln Asn Leu Arg Asp Gln Val
    200                 205                 210

GAT TAT GCA TTA GAT CAA GGA GCA GCG ATA TTT GTT AGT GAA TGG GGG    768
Asp Tyr Ala Leu Asp Gln Gly Ala Ala Ile Phe Val Ser Glu Trp Gly
215                 220                 225                 230

ACA AGT GCA GCT ACA GGT GAT GGT GGT GTG TTT TTA GAT GAA GCA CAA    816
Thr Ser Ala Ala Thr Gly Asp Gly Gly Val Phe Leu Asp Glu Ala Gln
                235                 240                 245
```

FIGURE 3C

```
GTG TGG ATT GAC TTT ATG GAT GAA AGA AAT TTA AGC TGG GCC AAC TGG        864
Val Trp Ile Asp Phe Met Asp Glu Arg Asn Leu Ser Trp Ala Asn Trp
            250                 255                 260

TCT CTA ACG CAT AAG GAT GAG TCA TCT GCA GCG TTA ATG CCA GGT GCA        912
Ser Leu Thr His Lys Asp Glu Ser Ser Ala Ala Leu Met Pro Gly Ala
            265                 270                 275

AAT CCA ACT GGT GGT TGG ACA GAG GCT GAA CTA TCT CCA TCT GGT ACA        960
Asn Pro Thr Gly Gly Trp Thr Glu Ala Glu Leu Ser Pro Ser Gly Thr
            280                 285                 290

TTT GTG AGG GAA AAA ATA AGA GAA TCA GCA TCT ATT CCG CCA AGC GAT       1008
Phe Val Arg Glu Lys Ile Arg Glu Ser Ala Ser Ile Pro Pro Ser Asp
295                 300                 305                 310

CCA ACA CCG CCA TCT GAT CCA GGA GAA CCG GAT CCA GGA GAA CCG GAT       1056
Pro Thr Pro Pro Ser Asp Pro Gly Glu Pro Asp Pro Gly Glu Pro Asp
            315                 320                 325

CCA ACG CCC CCA AGT GAT CCA GGA GAG TAT CCA GCA TGG GAT TCA AAT       1104
Pro Thr Pro Pro Ser Asp Pro Gly Glu Tyr Pro Ala Trp Asp Ser Asn
            330                 335                 340

CAA ATT TAC ACA AAT GAA ATT GTG TAT CAT AAC GGT CAG TTA TGG CAA       1152
Gln Ile Tyr Thr Asn Glu Ile Val Tyr His Asn Gly Gln Leu Trp Gln
            345                 350                 355

GCG AAA TGG TGG ACA CAA AAT CAA GAG CCA GGT GAC CCA TAC GGT CCG       1200
Ala Lys Trp Trp Thr Gln Asn Gln Glu Pro Gly Asp Pro Tyr Gly Pro
            360                 365                 370

TGG GAA CCA CTC AAA TCT GAC CCA GAT TCA GGA GAA CCG GAT CCA ACG       1248
Trp Glu Pro Leu Lys Ser Asp Pro Asp Ser Gly Glu Pro Asp Pro Thr
375                 380                 385                 390

CCC CCA AGT GAT CCA GGA GAG TAT CCA GCA TGG GAT TCA AAT CAA ATT       1296
Pro Pro Ser Asp Pro Gly Glu Tyr Pro Ala Trp Asp Ser Asn Gln Ile
            395                 400                 405

TAC ACA AAT GAA ATT GTG TAC CAT AAC GGC CAG CTA TGG CAA GCA AAA       1344
Tyr Thr Asn Glu Ile Val Tyr His Asn Gly Gln Leu Trp Gln Ala Lys
            410                 415                 420

TGG TGG ACA CAA AAT CAA GAG CCA GGT GAC CCA TAT GGT CCG TGG GAA       1392
Trp Trp Thr Gln Asn Gln Glu Pro Gly Asp Pro Tyr Gly Pro Trp Glu
            425                 430                 435

CCA CTC AAT TAA                                                        1404
Pro Leu Asn
440
```

(2) INFORMATION FOR SEQ ID NO: 2:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO: 2:

FIGURE 3D

```
Met Lys Lys Ile Thr Thr Ile Phe Ala Val Leu Leu Met Thr Leu Ala
-26 -25              -20                  -15

Leu Phe Ser Ile Gly Asn Thr Thr Ala Ala Asp Asp Tyr Ser Val Val
-10              -5                   1                   5

Glu Glu His Gly Gln Leu Ser Ile Ser Asn Gly Glu Leu Val Asn Glu
            10              15                   20

Arg Gly Glu Gln Val Gln Leu Lys Gly Met Ser Ser His Gly Leu Gln
         25                  30                  35

Trp Tyr Gly Gln Phe Val Asn Tyr Glu Ser Met Lys Trp Leu Arg Asp
     40                  45                  50

Asp Trp Gly Ile Thr Val Phe Arg Ala Ala Met Tyr Thr Ser Ser Gly
 55                  60                  65                  70

Gly Tyr Ile Asp Asp Pro Ser Val Lys Glu Lys Val Lys Glu Thr Val
             75                  80                  85

Glu Ala Ala Ile Asp Leu Gly Ile Tyr Val Ile Ile Asp Trp His Ile
             90                  95                 100

Leu Ser Asp Asn Asp Pro Asn Ile Tyr Lys Glu Glu Ala Lys Asp Phe
        105                 110                 115

Phe Asp Glu Met Ser Glu Leu Tyr Gly Asp Tyr Pro Asn Val Ile Tyr
120                 125                 130

Glu Ile Ala Asn Glu Pro Asn Gly Ser Asp Val Thr Trp Asp Asn Gln
135                 140                 145                 150

Ile Lys Pro Tyr Ala Glu Glu Val Ile Pro Val Ile Arg Asp Asn Asp
                155                 160                 165

Pro Asn Asn Ile Val Ile Val Gly Thr Gly Thr Trp Ser Gln Asp Val
            170                 175                 180

His His Ala Ala Asp Asn Gln Leu Ala Asp Pro Asn Val Met Tyr Ala
        185                 190                 195

Phe His Phe Tyr Ala Gly Thr His Gly Gln Asn Leu Arg Asp Gln Val
    200                 205                 210

Asp Tyr Ala Leu Asp Gln Gly Ala Ala Ile Phe Val Ser Glu Trp Gly
215                 220                 225                 230

Thr Ser Ala Ala Thr Gly Asp Gly Gly Val Phe Leu Asp Glu Ala Gln
            235                 240                 245

Val Trp Ile Asp Phe Met Asp Glu Arg Asn Leu Ser Trp Ala Asn Trp
        250                 255                 260

Ser Leu Thr His Lys Asp Glu Ser Ser Ala Ala Leu Met Pro Gly Ala
    265                 270                 275

Asn Pro Thr Gly Gly Trp Thr Glu Ala Glu Leu Ser Pro Ser Gly Thr
    280                 285                 290

Phe Val Arg Glu Lys Ile Arg Glu Ser Ala Ser Ile Pro Pro Ser Asp
295                 300                 305                 310
```

FIGURE 3E

Pro Thr Pro Pro Ser Asp Pro Gly Glu Pro Asp Pro Gly Glu Pro Asp
            315             320             325

Pro Thr Pro Pro Ser Asp Pro Gly Glu Tyr Pro Ala Trp Asp Ser Asn
            330             335             340

Gln Ile Tyr Thr Asn Glu Ile Val Tyr His Asn Gly Gln Leu Trp Gln
        345             350             355

Ala Lys Trp Trp Thr Gln Asn Gln Glu Pro Gly Asp Pro Tyr Gly Pro
    360             365             370

Trp Glu Pro Leu Lys Ser Asp Pro Asp Ser Gly Glu Pro Asp Pro Thr
375             380             385             390

Pro Pro Ser Asp Pro Gly Glu Tyr Pro Ala Trp Asp Ser Asn Gln Ile
            395             400             405

Tyr Thr Asn Glu Ile Val Tyr His Asn Gly Gln Leu Trp Gln Ala Lys
            410             415             420

Trp Trp Thr Gln Asn Gln Glu Pro Gly Asp Pro Tyr Gly Pro Trp Glu
        425             430             435

Pro Leu Asn
    440

MODIFIED TARGET ENZYMES HAVING CATALYTIC TRIADS AND USES THEREOF

The present application claims priority benefit under 35 U.S.C. §120, to U.S. Provisional Patent Application Ser. No. 60/268,347, filed Feb. 12, 2001, now abandoned.

FIELD OF THE INVENTION

This invention relates generally to modified target molecules which include a catalytic triad structure that alters the performance of the molecule. More particularly, such modified target molecules of the invention comprise genetically modified enzymes which include a catalytic triad structure that, among other things, can function in altering the pH profile of the enzyme. The invention also relates to methods of making and using such modified target molecules.

BACKGROUND OF THE INVENTION

Polypeptides comprise a wide variety of biological molecules, each having specific amino acid sequence, structure, and function. Most polypeptides interact with specific substances to carry out the function of the polypeptide. For instance, enzymes such as subtilisin or amylase interact with and hydrolyze specific substrates whereas proteinaceous cytokines or hormones typically interact with specific receptors to regulate, for example, growth or metabolism.

Efforts have been undertaken to alter characteristics or functional properties of various polypeptides by modifying the polypeptides' respective amino acid sequences. One approach has been to substitute one or more amino acids in the sequence of a polypeptide with a different amino acid(s) using in vitro mutagenesis techniques. As reported in the literature, such methods have been conducted to improve thermal or oxidative stability of various polypeptides. [See, e.g., Villafranca et al., *Science*, 222:782–788 (1983); Perry et al., *Science*, 226:555–557 (1984); Estell et al., *J. Biol. Chem*, 260:6518–6521 (1985); Rosenburg et al., *Nature*, 312:77–80 (1984); Courtney et al., *Nature*, 313:149–157 (1985)]. In addition, such methods have been reportedly used to generate enzymes with altered substrate specificities [See, e.g., Estell et al., *Science*, 223:655–663 (1986); Craik et al., *Science*, 228:291–297 (1985); Wells et al., *Proc. Natl. Acad. Sci.*, 84:1219–1223 (1987)].

The structural biology of various enzymes has also been examined in the literature in an effort to better understand enzyme catalysis. For instance, studies using recombinant DNA techniques to explore which residues are important for the catalytic activity of amylases and/or to explore the effect of modifying certain amino acids within the active site of various amylases and glycosylases have been conducted by various researchers [Vihinen et al., *J. Biochem.*, 107:267–272 (1990); Holm et al., *Protein Engineering*, 3:181–191 (1990); Takase et al., *Biochemica et Biophysica Acta*, 1120:281–288 (1992); Matsui et al., *Febs Letters*, 310:216–218 (1992); Matsui et al., *Biochemistry*, 33:451–458 (1992); Sogaard et al., *J. Biol. Chem.*, 268: 22480–22484 (1993); Sogaard et al., *Carbohydrate Polymers*, 21:137–146 (1993); Svensson, *Plant Mol. Biol.*, 25:141–157 (1994); Svensson et al., *J. Biotech.*, 29:1–37 (1993)].

Various members of the cellulase family of enzymes have also been examined by way of structural studies. Davies et al., *Biochemistry*, 37:1926–1932 (1998) describe the crystallography analysis of endoglucanase, Cel5A, from the alkalophilic *Bacillus agaradherans*. Davies et al. identified the structure of the catalytic core of this enzyme by multiple isomorphous replacement. The authors report that Cel5A performs catalysis via a double-displacement mechanism and that the Bronsted acid/base and enzymatic nucleophile in the catalytic core of Cel5A are residues Glu139 and Glu228, respectively. [See also, Davies et al., *Biochemistry*, 37:11707–11713 (1998)].

Additional enzymes which have been studied are the serine proteases and hen egg white lysozyme ("HEWL"). Analyses of various serine proteases have revealed that these enzymes contain a triad of the residues Asp-His-Ser in the active site [Matthews et al., *Nature*, 214:652–656 (1967); Blow et al., *Nature*, 221:337 (1969)] and tend to have pH optima in the neutral to alkaline range [Dodson et al., *Trends Biochem. Sci.*, 23:347 (1998)]. This type of triad has been observed in a number of diverse enzymes. Variations within such triads, however, have been described that catalyse the hydrolysis of many classes of substrates [Dodson et al., supra].

In the serine proteases, the triad in the active site can act as a charge-relay system [Blow et al., supra], wherein the histidine residue removes a proton from the serine residue to make it a more potent nucleophile. In this catalytic scheme, the formation of an unusually short catalytic hydrogen bond between the histidine and aspartate appears to be critical so as to make the histidine a more potent base by facilitating its deprotonation of serine. [Wang et al., *J. Biol. Chem.*, 268: 14096–14102 (1993)] This hydrogen has recently been visualized in an ultra-high resolution x-ray study of subtilisin [Kuhn et al., *Biochemistry*, 37:13446 (1998)].

HEWL contains two catalytic carboxylates, aspartate and glutamate, in the active-site [see, e.g., Blake et al., *Nature*, 206:757 (1965); Johnson et al., *Nature*, 206:761 (1965); Phillips, *Harvey Lectures*, 66:135 (1971); Ford et al., *J. Mol. Biol.*, 88:349 (1974); Kelly et al., *Nature:*282:875 (1979)]. The glutamate residue in that active-site acts as an acid/base catalyst, initially protonating the glycosidic bond and catalysing bond fission. The aspartate residue in that active-site facilitates the reaction by stabilizing the resulting carbonium ion intermediate.

Similar to HEWL, various other enzymes have been reported to contain two carboxylates for catalysis, including certain acid proteases like the pepsin family [see, Hsu et al., *Nature*, 266:140–145 (1977)], certain retro-viral proteases [see, Miller et al., *Nature*, 337:576 (1989)], and the family of glucosyl hydrolases [see, Davies et al., *Structure*, 3:853 (1995); White et al., *Curr. Op. Struct. Biol.*, 7:645 (1997)]. The pKa of a glutamate side-chain in solution is approximately 4.5, and as the acid/base group has to be protonated in the resting state, most of these types of enzymes tend to perform or have activity in acidic environments [White et al., supra]. However, some of these types of enzymes which utilize a dicarboxylate catalysis mechanism have pH optima in the neutral to alkaline range. To date, it has not been fully understood how such enzymes may accomplish such an increase in the pKa of the acid/base carboxylate group.

SUMMARY OF THE INVENTION

As described herein, Applicants have identified the structure of the catalytic core of cellulase 103 from an alkalophilic *Bacillus* sp. Cellulase 103 is a glycoside hydrolase family 5 (GH-5) enzyme, isolated from an alkaline *Bacillus* sp., found in soda lakes [Pennisi, *Science*, 276:705 (1997)]. Cellulase 103, in its isolated native sequence form, is an alkaline cellulase with a pH optimum of about 8.0. The folding motif of the enzyme's catalytic core was identified as a (beta/alpha)$_8$ barrel, and the conserved active-site residues are found in a deep cleft at the carboxy end of the beta-sheet. In GH-5 enzymes generally, a glutamate in the active-site is the nucleophile [Wang et al., *J. Biol. Chem.*, 268:14096–14102 (1993)].

Applicants surprisingly found that such cellulase 103 contains a catalytic triad comprising residues Ser227, His200, and Glu139, and based on amino acid sequence structure and functional analyses, it is believed that this catalytic triad functions, at least in part, to raise the pKa of its acid/base catalyst residue, Glu139. By enabling the Glu139 residue to act as an acid/base catalyst at a pH well above its normal pKa, the cellulase 103 enzyme can function at a higher pH. In the case of cellulase 103, this catalytic triad is believed to allow the enzyme to efficiently hydrolyse cellulose under alkaline conditions.

Having identified such a structure and its function, Applicants provide in the present invention modified target molecules comprising polypeptides which have been genetically engineered or modified to include a catalytic triad that alters the performance of the polypeptide, and preferably, to include a catalytic triad that alters the pH profile of the polypeptide. Optionally, the modified target molecule has an acidic pH profile as compared to its precursor having an alkaline pH profile. In a preferred embodiment, the modified target molecule has a relatively alkaline pH profile as compared to its precursor having a more acidic pH profile. Optionally, the modified target molecule is a modified target enzyme, wherein the modified target enzyme is active or stable in a pH range of about 7.0 to about 14.0, and preferably, in a pH range of 7.0 to 10.0, in contrast to its precursor having activity or stability at acidic pH below 7 (for example, pH of 0 to 6.99). In a particularly preferred embodiment, the genetically modified target enzyme comprises a substitution, deletion or addition of amino acid residue(s) equivalent to one or more of amino acid residues Serine 227, Histidine 200, or Glutamate 139 in the Bacillus cellulase 103 sequence (FIGS. 3A–3E; SEQ ID NO:2). In an even more preferred embodiment, such genetic modification comprises a substitution, deletion or addition of one or more amino acid residues so that the modified target enzyme comprises a catalytic triad containing three amino acid residues equivalent to amino acid residues Serine 227, Histidine 200 and Glutamate 139, respectively, in the Bacillus cellulase 103 sequence (FIGS. 3A–3E, SEQ ID NO:2).

In one embodiment of the invention, there is provided a method of producing such modified target molecules comprising the steps of providing a target molecule; analyzing said target molecule to identify one or more regions or amino acid residues in the target molecule to be genetically modified, wherein said one or more regions or residues correspond to or are equivalent to the residues in the catalytic triad of cellulase 103; modifying said one or more regions or amino acid residues so as to form a catalytic triad in the target molecule; and selecting modified target molecules having an altered performance profile. Modified target molecules produced by these methods herein are further provided. Optionally, the modified target molecules produced in accordance with such methods have a pH profile which differs from the pH profile of the target or precursor molecule.

In one particular embodiment, there is provided a method of producing a modified target molecule having an altered performance profile, comprising the steps of:

(a) providing a target molecule;
(b) analyzing said target molecule to identify one or more regions or amino acid residues in the target molecule for modification;
(c) modifying said one or more regions or amino acid residues identified in the target molecule so as to introduce a catalytic triad in the target molecule, wherein said catalytic triad includes a first member comprising an amino acid residue or chemical group which acts as a proton donor, a second member which is equivalent to histidine 200 in the sequence of Bacillus cellulase 103 (SEQ ID NO:2), and a third member which is an equivalent to serine 227 in the sequence of Bacillus cellulase 103 (SEQ ID NO:2); and
(d) selecting a modified target molecule having an altered performance profile as compared to the target molecule of (a). Optionally, the first, second and third members of the catalytic triad of step (c) include amino acid residues equivalent to glutamine 139, histidine 200 and serine 227, respectively, in the sequence of Bacillus cellulase 103 (SEQ ID NO:2).

In another particular embodiment, there is provided a method of producing a modified target molecule having an altered performance profile, comprising the steps of:

(a) providing a target molecule;
(b) analyzing said target molecule to identify one or more regions or amino acid residues in the target molecule for modification so as to introduce a catalytic triad;
(c) genetically modifying DNA encoding said one or more regions or amino acid residues identified in the target molecule so as to create a library of modified target molecules having mutations; and
(d) selecting a modified target molecule from said library having an altered performance profile as compared to the target molecule of (a). The target molecule may be an enzyme, and more particularly, may be a hydrolase. A library of modified target molecules produced in accordance with this method is further provided.

In another particular embodiment, there is provided a modified target molecule comprising a polypeptide genetically modified to comprise a catalytic triad that alters the performance of the polypeptide, wherein said catalytic triad comprises a first member, a second member and a third member and said first member is a proton donor, said second member is equivalent to the Histidine 200 residue in the Bacillus cellulase 103 sequence (SEQ ID NO:2), and said third member is equivalent to the Serine 227 residue in the Bacillus cellulase 103 sequence (SEQ ID NO:2).

In another embodiment, the present invention provides nucleic acid molecules comprising DNA which encodes the modified target molecules of the invention.

In another embodiment, the present invention provides expression vectors incorporating DNA which encodes the modified target molecules according to the invention, as well as host cells into which such DNA and/or expression vectors have been transformed or transfected. In a further embodiment, the invention provides methods for making the modified target molecules described herein, comprising expressing DNA encoding the modified target molecules of the invention or an expression vector incorporating such DNA in a host cell. Optionally, the methods for making the modified target molecules comprise the steps of providing a target molecule; analyzing said target molecule to identify one or more regions or amino acid residues in the target molecule to be genetically modified, wherein said one or more regions or residues correspond to or are equivalent to the residues in the catalytic triad of cellulase 103; modifying said one or more regions or amino acid residues so as to form a catalytic triad in the target molecule; selecting modified target molecules having an altered performance profile, and expressing DNA encoding the modified target molecules or an expression vector incorporating such DNA in a host cell.

In another embodiment, the invention provides laundry or dishwashing detergent compositions which incorporate the modified target molecules according to the invention. In another embodiment, the present invention provides textile desizing compositions which incorporate the modified target molecules according to the invention.

In a further embodiment of the invention, a method of laundering clothing or washing dishes with a dishwashing detergent composition which incorporates a modified target molecule according to the invention is provided. In another embodiment of the present invention, a method of desizing textiles with a composition which incorporates a modified target molecule according to the invention is provided.

In another embodiment, the invention provides therapeutic or diagnostic compositions which incorporate the modified target molecules according to the invention. Such therapeutic or diagnostic compositions will have a variety of uses in the health care industry, and may comprise various components such as buffers, carriers, etc.

A need exists in the art for novel and improved enzymes which have altered performance profiles to facilitate their use in various commercial processes and industrial applications, as well as therapeutic or diagnostic applications in the health care field. For example, a molecule or enzyme having desirable properties or characteristics, but somehow limited in its use due to an acidic pH profile, can be modified using the present inventive methods to successfully alter the pH profile of the molecule so that it is active or stable under alkaline (or physiologically acceptable) pH conditions. Alternatively, the methods of the invention can be employed to change an enzyme's alkaline pH profile to an acidic pH profile.

BRIEF DESCRIPTION OF THE DRAWINGS

FIGS. 1A–1C show the stereoviews of the structure of the domain comprising the catalytic triad of cellulase 103 and comparison of the catalytic triads found in various other GH5 enzymes. 1A. The electron density map of the active-site, including the catalytic triad, after heavy-atom refinement and phasing using SHARP, and subsequent density modification using SOLOMON. 1B. Ribbons diagram of the tertiary structure, with the catalytic triad and the Glu nucleophile illustrated as ball and stick. 1C. Close up of the catalytic triad and the nucleophile Glu.

FIG. 2A illustrates the Type A catalytic triad found in cellulase 103;

FIG. 2B illustrates the Type B catalytic triad found in exo-1,3-glucanase from *Candida albicans* [Cutfield et al., *J. Mol. Biol.*, 294:771–783 (1999)];

FIG. 2C illustrates the Type C catalytic triad found in endo-1,4-glucanase from *Acidothermus cellulyticus* [Sakon et al., *Biochemistry*, 35:10648–10660 (1996)].

FIGS. 3A–3E illustrates the DNA sequence (SEQ ID NO:1) of the gene for Bacillus cellulase 103 and its putative amino acid sequence (SEQ ID NO:2).

DETAILED DESCRIPTION OF THE INVENTION

I. Definitions

"Target molecule", "target", or "precursor" refers to any molecule which includes or utilizes one or more chemical groups as a proton donor. Optionally, the target molecule is an enzyme, and the enzyme comprises an active site that includes at least one chemical group or amino acid residue which acts as a proton donor in catalysis. The target enzyme may optionally utilize a proton donor which corresponds to or is equivalent to the glutamate residue at position 139 in the sequence of Bacillus cellulase 103, shown in FIGS. 3A–3E (SEQ ID NO:2). Preferably, the target enzyme includes a carboxylic acid in the active site which acts as the proton donor, and more preferably, the target enzyme further includes a beta/alpha or "TIM" barrel fold (the beta/alpha barrel is typically made of a series of parallel beta-strands which are interconnected by alpha-helices). Examples of target enzymes contemplated by the invention include but are not limited to hydrolases and transferases, particularly hydrolases that include two carboxylic acids in the respective enzyme's active site wherein one of the carboxylic acids is a proton donor and the other carboxylic acid is a nucleophile. Various types of hydrolases include cellulases and proteases. Further examples of such target enzymes include pepsins, amylases, esterases, galactosidases, nucleases, and polymerases. The target molecule may be isolated or purified from any native source or produced by any chemical synthesis technique or recombinant method. The target molecule may comprise a wild-type (native-sequence) polypeptide derived from nature and includes naturally-occurring truncated or secreted forms, naturally occurring variant forms and naturally occurring allelic variants. Suitable sources of target molecules are prokaryotic or eukaryotic organisms, including fungi, bacteria, plants or animals.

A "modified target molecule", "mutant target molecule", or "variant target molecule" is a target molecule which has been subjected to genetic or chemical modification so as to change its biochemical, structural or physico-chemical properties. A "genetic modification" in a target molecule (i.e., a genetically modified target molecule) means that the DNA sequence encoding a target molecule has been modified to produce a mutant DNA sequence which encodes the substitution, addition or deletion of one or more amino acids in the target molecule sequence as compared to its precursor. The "modification" in the target molecule is intended to cause or result in a change in the characteristics of the molecule so as to alter the pH profile or performance of the molecule as compared to its respective precursor. Such modification is generally of the target DNA sequence which encodes the amino acid sequence of the target rather than manipulation of the target polypeptide per se. By "altering the performance" is intended to mean the stability (e.g., oxidative or thermal) or the activity (e.g., the rate or efficiency with which the modified target molecule hydrolyzes substrate) of the molecule in its various applications and uses. In a preferred embodiment, the modification is a genetic modification which introduces or results in a catalytic triad, as defined below, in a target enzyme. In a particularly preferred embodiment, such genetic modification comprises a substitution, deletion or addition of amino acid residue(s) equivalent to one or more amino acids of the Bacillus cellulase 103 sequence (FIGS. 3A–3E; SEQ ID NO:2). In an even more preferred embodiment, such genetic modification comprises a substitution, deletion or addition of one or more amino acid residues so that the modified target enzyme comprises a catalytic triad containing a first member, second member, and third member equivalent to amino acid residues Serine 227, Histidine 200 and Glutamate 139, respectively, in the Bacillus cellulase 103 sequence (FIGS. 3A–3E, SEQ ID NO:2). In another preferred embodiment, such genetic modification comprises a substitution, deletion or addition of one or more residues so that the modified target enzyme comprises a catalytic triad containing (1) a proton donor equivalent to Glutamate 139 in the Bacillus cellulase 103 sequence (FIGS. 3A–3E, SEQ ID NO:2), (2) a residue equivalent to Histidine 200 in the Bacillus cellulase 103 sequence (FIGS. 3A–3E, SEQ ID NO:2), and (3) a water molecule which functions in acid/base catalysis.

"Catalytic triad" refers to a structure in the active site of an enzyme that includes three member molecules which function in acid/base catalysis. Typically, such three member molecules will include either three hydrogen bonded amino acid residues which function in acid/base catalysis, or two hydrogen bonded amino acid residues associated with a water molecule which function in acid/base catalysis. The three members of the catalytic triad are typically not contiguous in the primary sequence of the enzyme; rather the members of the catalytic triad will typically form a hydrogen bonded structure in the three dimensional structure of the enzyme. As used herein, the term "catalytic triad" refers to a structure that includes a first member, a second member and a third member. The first member is an amino acid residue or chemical group which acts as the proton donor. Typically, such first member comprises a glutamate or aspartate residue which acts as a proton donor. The second and third members in the triad act in the charge relay mechanism. Optionally, the second member is an amino acid residue which corresponds to or is equivalent to the histidine 200 residue in cellulase 103. Optionally, the third member is an amino acid residue which corresponds to or is equivalent to the serine 227 residue of cellulase 103. The third member may optionally be a serine, threonine, or aspartate residue, and preferably such serine, threonine or aspartate residue 5 corresponds to or is equivalent to such a residue located N-terminal to the acid/base catalyst (such as glu228). In an alternative embodiment, the third member may be an asparagine or aspartate residue, such as an asparagine or aspartate residue corresponding to or equivalent to such residues located on a beta-strand adjacent to Ser227. In yet a further alternative embodiment, the third member is a water molecule which functions in acid/base catalysis. As disclosed herein, the catalytic triad in cellulase 103 consists of residues Serine 227, Histidine 200 and Glutamate 139. In a preferred embodiment, the catalytic triad of the invention comprises three members equivalent to Serine 227, Histidine 200 and Glutamate 139, respectively, of cellulase 103. Preferably, the catalytic triad consists of (1) a proton donor which is functionally equivalent to the Glutamate 139 residue of cellulase 103, (2) a second member equivalent to Histidine 200 of cellulase 103 and (3) a third member equivalent to Serine 227 of cellulase 103, wherein the second and third members of the triad act in the charge relay mechanism. More preferably, the catalytic triad comprises three members equivalent to Serine 227, Histidine 200 and Glutamate 139, respectively, of cellulase 103 and functions by way of a charge relay mechanism in which the pKa of the acid/base catalyst is increased, and even more preferably, functions by way of a charge relay mechanism wherein the pKa of the nucleophile is decreased simultaneously while the pKa of the acid/base catalyst is increased. Optionally, the catalytic triad functions to increase the pKa of the acid/base catalyst sufficiently to allow protonation of the substrate. Preferably, the catalytic triad functions to increase the pKa of the acid/base catalyst such that the modified target enzyme has an alkaline pH profile.

Members of the catalytic triad or residues may be determined to be an "equivalent" if such members or residues are structurally analogous to cellulase 103 by way of primary sequence or tertiary structure or if they are functionally equivalent. A member or residue of a target molecule is considered equivalent to a residue of Bacillus cellulase 103 if it is either homologous (i.e., corresponds in position for either the primary or tertiary structure) or analogous to a specific residue or portion of that residue in Bacillus cellulase 103 (i.e., having the same or similar functional capacity to combine, react, or interact chemically or structurally).

"Alkaline pH profile" refers to a pH profile of an enzyme wherein the maximum activity of the enzyme occurs in a pH range from about 7.0 to about 14.0, optionally, from 7.0 to 14.0.

"Acidic pH profile" refers to a pH profile of an enzyme wherein the maximum activity of the enzyme occurs in a pH range from 0 to about 7.0, optionally, from 0 to 6.99.

"Expression vector" means a DNA construct comprising a DNA sequence which is capable of effecting the expression of said DNA in a suitable host, generally being operably linked to a suitable control sequence. Such control sequences may include a promoter to effect transcription, an optional operator sequence to control such transcription, a sequence encoding suitable mRNA ribosome-binding sites, and sequences which control termination of transcription and translation. The vector may be a plasmid, a phage particle, or DNA intended to effect genomic insertion, i.e., integration. Once transformed into a suitable host, the vector may replicate and function independently of the host genome, or may, in some instances, integrate into the genome itself. Plasmid and vector are sometimes used interchangeably as the plasmid is the most commonly used form of vector at present. However, the invention is intended to include such other forms of expression vectors which serve equivalent functions and which are known in the art, particularly including phage display.

"Host strain" or "host cell" means a suitable host for, e.g., an expression vector comprising DNA encoding the modified target molecule according to the present invention. Host cells useful in the present invention are generally prokaryotic or eukaryotic hosts, including any transformable microorganism in which the expression of a modified target molecule according to the present invention can be achieved. Specifically, host strains of the same species or genus from which the modified target molecule is derived are suitable, such as a Bacillus strain. Host cells may be transformed or transfected with vectors constructed using recombinant DNA techniques known in the art. Such transformed host cells are capable of either replicating vectors encoding the modified target molecule or expressing the desired modified target molecule.

"Isolated" when used herein to describe various molecules means a molecule, such as a polypeptide, which has been identified and separated and/or recovered from a component of its natural environment. Contaminant components of its natural environment are materials that would typically interfere with the activity of the molecule. Preferably, an isolated molecule will be prepared by at least one purification step.

Abbreviations used herein, particularly three letter or one letter notations for amino acids are described in Dale, J. W., Molecular Genetics of Bacteria, John Wiley & Sons, (1989) Appendix B. References in the specification to residues found in the sequence of cellulase 103 may employ various numbering and notations such as "glutamate 139" or "glu139" and refer to those respective amino acid positions shown in FIGS. 3A–3E (SEQ ID NO:2).

II. Methods and Materials

As described in further detail in the Example below, Applicants have identified the crystal structure of cellulase 103, and particularly, have identified that the catalytic triad of cellulase 103 consists of three hydrogen-bonded residues, glutamate 139, histidine 200, and serine 227. To elucidate the function of this catalytic triad, Applicants conducted an analysis of the structural and functional characteristics between cellulase 103 and various other GH-5 cellulases. The analysis revealed that the catalytic triad may comprise various member molecules, and as described in the Example section, Applicants have referred to certain of the catalytic triads as type "A", type "B", and type "C".

As Applicants have identified in the structure of cellulase 103, the serine at position 227 hydrogen-bonds to the histidine in the active-site to form a catalytic triad. At higher pH, the histidine side-chain will be deprotonated. Typically, although the histidine residue may act as a hydrogen donor in this state, it cannot act as a proton donor. When simultaneously hydrogen bonded to the serine residue at position 227, however, the histidine residue can act as a proton donor if it simultaneously removes a proton from the serine. Accordingly, the serine residue enables the histidine to act as a proton donor to glutamate 139. It is presently believed that this may maintain protonation of glutamate 139 at a pH above its pKa, i.e., the apparent pKa is raised.

At least one consequence of this reaction is that the serine residue at position 227 becomes, transiently, negatively charged. Transient generation of negative charge in the interior may be advantageous. After protonation, the nucleophile glutamate 228 forms a covalent glucosyl intermediate. The reaction is subsequently completed by hydrolysis of the intermediate by a hydroxyl ion. The hydroxyl ion is generated by removal by glutamate 139 of a proton from water, i.e., it now acts as a base, and the glutamate then returns to its resting state [Davies et al., *Biochemistry*, 37:11707 (1998)]. The development of an unfavorable interior negative charge on serine 227 would be expected to favor a rapid reprotonation. In this proposed reaction, the protonation state of the glutamate and the histidine in the catalytic triad do not change. Essentially, a proton from the buried serine 227 is "relayed" to the catalytic glutamate 139 via histidine 200.

The pH profile of the threonine containing sub-family 5-2 cellulase from *Bacillus subtilis* (BSC) has been determined by Park et al., *Protein Engineering*, 6:921 (1993), and the activity optimum is at pH 5.0. Park et al. also determined the pH profile of cellulase NK1, a sub-family 5-2 cellulase from an alkalophilic Bacillus, which has a serine residue equivalent to position 227 in cellulase 103. The NK1 cellulase has a broad pH profile with an optimum around 9.5, and is highly active at pH 10. Site specific mutagenesis suggests that serine 287 and alanine 296 of NK1 cellulase are important in alkaline activity [Park et al., supra]. However, mutation of both together, to their equivalents in the BSC native sequence, did not shift the pH profile entirely to that of BSC. Further, mutation of these sites in BSC to their equivalents in NK1 cellulase did not shift the pH profile of BSC to that of NK1 cellulase [Park et al., supra].

Based on Applicants' analyses described herein, it is believed that the difference between the acid and alkaline profiles of the various enzymes is the presence of certain catalytic triads, as described and defined herein.

In accordance with these findings, the present invention provides compositions comprising modified target molecules and methods for making modified target molecules which comprise a catalytic triad that alters the performance of the molecule. It is contemplated that the methods of the present invention can be conducted using various target molecules. Preferably, the target molecule is an enzyme, and more preferably, is an enzyme comprising an active site that includes at least one chemical group or amino acid residue which acts as a proton donor. The target enzyme is preferably modified to modulate the chemical group or residue(s) which act as a proton donor and that will result in an altered pH profile as compared to its precursor. More preferably, the modified target enzyme will have a pH profile such that it is active or stable in alkaline conditions, i.e., at pH of about 7 or greater than 7. Preferably, the target molecule is a hydrolase.

In the methods of the invention, a target molecule is provided and analyzed to identify regions within the molecule or particular amino acid residues within the target molecule that may be modified so as to introduce a catalytic triad, as defined herein, into the target molecule. Preferably, amino acid residue(s) in the target identified for modification correspond to or are equivalent to those residues in cellulase 103 which act as the catalytic triad. Alternatively, regions in the target can be identified for modification that correspond to those regions in cellulase 103 which contain the residues that form the catalytic triad in cellulase 103. Regions in the target identified for modification may, for instance, may comprise a particular contiguous sequence of residues in the primary sequence of the target or comprise a two- or three-dimensional space of the structure of the target.

As shown in FIGS. 1 and 2, the structure of cellulase 103 reveals that the folding motif of the enzyme's catalytic core is a (beta/alpha)$_8$ barrel, and the active-site residues are found in a deep cleft at the carboxy end of the beta-sheet. The beta/alpha barrel is made of a series of parallel beta-strands which are interconnected by alpha-helices. The acid/base catalyst in cellulase 103 is believed to be glutamate 139 and the nucleophile to be glutamate 228. The two carboxylate groups are approximately 5.0 Å apart. Adjacent to glutamate 139 is histidine 200, between which there is a short 2.77 Å hydrogen bond, between atoms OE2 and ND1. Also in close proximity to histidine 200 is serine 227, with a hydrogen bond between NE2 and OG of 2.71 Å.

To identify equivalent regions or residues in the target molecule, various types of comparative analyses between the target molecule and cellulase 103 can be conducted. In one embodiment, the sequence analysis may comprise a step-wise analysis wherein, in the comparison between the target sequence and the sequence of cellulase 103, the proton donor is first identified in the target. Typically, in a target enzyme, the proton donor will comprise a glutamate or aspartate residue. Preferably, the proton donor in the target molecule corresponds to or is equivalent to the glutamate 139 residue of cellulase 103. The residues which correspond to the second and third members of a catalytic triad (or regions which contain such residues) can then be identified. For those target molecules which are found to include a proton donor molecule but do not include any particular residues which correspond to the second or third member residues of the catalytic triad, such second or third member residues of the catalytic triad can be introduced into the sequence of the target by way of genetic modification, as described below.

The analysis of the target molecule may include various types of primary sequence or structural (e.g., secondary or tertiary) analysis. The primary amino acid sequence of a target molecule may be determined using routine techniques well known in the art. For instance, the target molecule may be isolated or purified and its DNA and/or amino acid sequences determined using routine chemical or genetic methods. The amino acid sequence of the target molecule can then be compared and aligned to the sequence of the Bacillus cellulase 103 sequence shown in FIGS. 3A–3E (SEQ ID NO:2). For example, the primary amino acid sequence of the target molecule may be analyzed for sequence homology to the sequence of cellulase 103. For purposes herein, the terms "homology" and "identity" are used interchangeably when referring to structural analyses. Techniques for conducting such sequence homology analysis are well known to those skilled in the art, and may be conducted, by way of example, using publicly available computer software programs such as BLAST, BLAST-2, Megalign (DNASTAR), and INHERIT. Sequence homology can be determined by aligning the sequences being compared and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full-length of the sequences being compared. Optionally, the algorithms utilized are those set to the default values by the publicly available software program. Sequence homology analysis can be used to determine, e.g., regions or amino acid residues which are conserved or not conserved between the aligned sequences.

Between certain families of target molecules or enzymes, homologies between the primary sequences of the family members can be relatively high. In those primary sequence alignments, conducted as described above, where it is found that the primary sequence of the target molecule has homology of about 70% or greater than 70% to the primary sequence of cellulase 103, it is believed that the residues or regions in the target which correspond to those of the catalytic triad in cellulase 103 can be identified with more particularly high precision, and in such instances, it may be desirable to introduce genetic modifications into the target sequence using more specific types of genetic engineering techniques such as site-directed mutagenesis.

Optionally, in those primary sequence alignments where it is found that the primary sequence of the target molecule has homology of less than about 70% to the primary sequence of cellulase 103, it may be desirable to conduct further secondary or tertiary structural analysis (such as described below) to identify residues or regions which correspond to or are equivalent to those of the catalytic triad in cellulase 103. Alternatively, in such instances, it may be desirable to modify regions (as opposed to specific residues) in the target molecule.

The structural analysis can also be performed by comparing secondary or tertiary structures of the target molecule with those of cellulase 103. The secondary or tertiary structure of a target molecule may be obtained by techniques known in the art, including those described in the Example below. For example, one can determine equivalent residues or regions by tertiary structure analysis of the crystal structures of the respective target molecule and cellulase 103 (as illustrated in FIGS. 1 and 2). Methods for crystallization and analysis of crystalline forms of molecules are known in the art and are further described in the Example below.

If the target molecule is a member of a well characterized family of molecules, one skilled in the art may conduct an analysis based on predicted common super-secondary structures between such family members. For example, several investigators have reported to predict common super-secondary structures between enzymes such as glucanases [MacGregor et al., *Biochem. J.*, 259:145–152 (1989)], within alpha-amylases and other starch-metabolizing enzymes [Jaspersen et al., *J. Prot. Chem.*, 12:791–805 (1993); MacGregor et al., *Starke*, 45:232–237 (1993)], and sequence similarities between enzymes with similar super-secondary structures to alpha-amylases [Janecek et al., *FEBS Letters*, 316:23–26 (1993); Janecek et al., *J. Prot. Chem.*, 12:509–514 (1993)]. These techniques may also be utilized to identify the regions which contain residue(s) of the active-site.

Comparisons of such structures of the target molecule to that of cellulase 103 can then be performed by aligning or superimposing the structures using, for instance, commercially available software programs such as Insight II, Quanta, O, and FRODO. Methods for superimposing such structures has been described in the literature, such as by Altamirano et al., *Nature*, 403:617–622 (2000) using the computer program SETOR. It is noted that a target molecule may not have a high degree of primary amino acid sequence homology to cellulase 103, but may be structurally homologous to cellulase 103 based on a comparison of all or part of the tertiary structure of the target molecule.

Using such methods, one skilled in the art, without undue experimentation, can then identify corresponding residues or regions in the target molecule which may be desirable to modify in order to introduce a catalytic triad structure into the target molecule.

Preferably, the tertiary structure of the target enzyme is determined and compared by computer software analysis to the structural region comprising the catalytic triad in Bacillus cellulase 103 (illustrated in FIGS. 1 and 2). As described herein, the catalytic triad region of the cellulase 103 peptide chain includes residues serine 227, histidine 200, and glutamine 139. The structures of the target molecule and cellulase 103 can then be superimposed and aligned, as described above, and residue(s) in the target molecule desirable to modify or mutate can be identified. Once identified, various combinations of amino acid substitutions, insertions or deletions can be made in the target sequence so as to introduce a catalytic triad in the target and then screened or tested, as described below, to ascertain which deletions, substitutions or insertions can be tolerated in the sequence to achieve the desired pH profile without adversely affecting other desired activity or functions of the molecule.

One approach in accomplishing such modifications may include combinatorial mutagenesis wherein residue(s) at a particular region or site in the target may be mutated and selected based on desired performance or pH profiles. In one embodiment of the methods of the invention, regions in the target molecule can be identified which include residues that may correspond to the first, second or third members of the catalytic triad. Optionally, "regions" in the target desired for modification can be defined in length of residues in the primary sequence or distances in the spaces between selected residues in the secondary or tertiary structure of the target. Such regions in the target can then be mutated to create libraries of modified target molecules having genetic modifications in specific loci relating to regions corresponding to the catalytic triad of cellulase 103. Such techniques have been described in the art, such as those wherein residues are mutagenized within particular loci or sites in a sequence of a target, and subsequently displayed using phagemid particles and selected based on desired performance profiles. [See e.g., Ruan et al., *Protein Science*, 7:2345–2353 (1998)].

Depending on the particular target molecule, one, two, three or more residues may be selected for modification. If a target molecule includes a proton donor residue in its sequence that, for example, corresponds to or is equivalent to glu139 in cellulase 103, and that same target molecule does not contain any residues which correspond to the second and third member residues of the catalytic triad, a desired modification may be an insertion of two amino acid residues into the target sequence to form a catalytic triad. That catalytic triad will consist of a first member, a second member and a third member, as defined herein. Optionally, the catalytic triad introduced into the target sequence will be structurally similar to any of those triad structures described in Marquart et al., *Acta Crystallographics*, B39:480–490 (1983). Such an insertion may comprise insertion of residues histidine or serine (or threonine) in the target sequence so as to form the catalytic triad, or insertion of residues which function similarly to such histidine or serine residues. In a preferred embodiment, the modifications selected for the target include a modification such that the modified target molecule includes a serine or threonine residue as an equivalent to the serine at position 227 of cellulase 103.

The desired modifications of the target molecules can be accomplished using standard techniques known in the art. For instance, amino acid substitutions, deletions or insertions in the target molecule can be accomplished using recombinant DNA technology. The modified target molecules can be prepared by introducing appropriate nucleotide changes into the target DNA, and/or by synthesis of the desired modified target molecule. Variations or modifications in the sequence of the target molecules described herein, can be made, for example, using any of the techniques for conservative and non-conservative mutations known in the art. Optionally, the modification is by substitution or addition of at least one amino acid with any other amino acid in one or more of the positions equivalent to serine 227, histidine 200 or glutamine 139 in cellulase 103. Amino acid substitutions can be the result of replacing one amino acid with another amino acid having similar structural and/or chemical properties, such as the replacement of a leucine with a serine, i.e., conservative amino acid replacements. The types of desired modifications may be further assessed by systematically making insertions, deletions or substitutions of amino acids in the target sequence and testing or assaying the resulting modified target molecules for activity or performance at an alkaline or acidic pH profile, as described below.

Methods for modifying genes encoding targets (i.e., through site-directed oligonucleotide mutagenesis) and transforming, expressing and secreting enzyme products produced pursuant to the mutagenized gene have been described in the art, including PCT Publication No. WO95/10603 (Novo Nordisk), PCT Publication No. WO94/02597 (Novo Nordisk), PCT Publication No. WO94/18314 (Genencor International, Inc.) and PCT Publication No. WO91/00353 (Gist Brocades). Additional suitable methods for manipulation of the precursor DNA sequence include methods disclosed herein and in commonly owned U.S. Pat. Nos. 4,760,025 and 5,185,258. Further methods for conducting still other types of mutagenesis and creation of libraries of mutagenized sequences are described by, e.g., Ruan et al., *Protein Science*, 7:2345–2353 (1998) (combinatorial mutagenesis); Carter et al., *Nucl. Acids Res.*, 13:4331 (1986); Zoller et al., *Nucl. Acids Res.*, 10:6487 (1987) (site-directed mutagenesis); Wells et al., *Gene*, 34:315 (1985) (cassette mutagenesis); Wells et al., *Philos. Trans. R. Soc. London SerA*, 317:415 (1986) (restriction selection mutagenesis) that can be performed on cloned DNA of the target to produce the modified target molecule DNA. For general reviews of techniques that may be employed in protein structural analysis and mutagenesis, see, e.g., *Protein Engineering and Design*, P. Carey, Ed., Academic Press (1996); *Rational Drug Design: Novel Methodology and Practical Applications*, A. Parrill and M. Reddy, Eds., American Chemical Society (1999).

To select for or determine the desired activity or properties of a modified target molecule, the modified target molecule can be tested or screened in various assays known in the art. For instance, a modified target enzyme according to the invention can be tested to determine its pH profile, as compared to its precursor. The assays conducted to determine the pH profiles may be specific to a particular target enzyme, and determining the appropriate assay for a specific enzyme can be determined by those skilled in the art. pH measurements can be made by the skilled artisan using standard techniques well known in the art. Preferably, a modified target enzyme comprises a modification which results in an alkaline pH profile as compared to its precursor which has an acidic pH profile. Optionally, however, the methods of the invention may be employed to alter the pH profile of a target molecule from an alkaline pH profile to an acidic pH profile.

It is contemplated that the modifications to a target molecule as described herein may also be effective in changing or improving the rate of catalytic efficiency of a modified target as compared to its precursor. Various assays known in the art may be conducted to compare the activities of a modified target molecule and its precursor at varying pH conditions. Such assays are available, for instance, as commercial assay kits, or as described in the art. For instance, U.S. Pat. No. 6,008,026 describes assays which may be conducted to determine amylase activity (rates of hydrolysis) and thermal stability; assays for measuring proteolytic activity are described, e.g., in Kalisz, "Microbial Proteinases", *Advances in Biochemical Engineering/Biotechnology*, A. Fiechter ed., 1988 and in U.S. Pat. No. 5,185,258; assays for measuring cellulase activities are described, e.g., in Ghose et al., *Pure & Appl. Chem.*, 59:257–268 (1987); and various assays are described in Stauffer, "Enzyme Assays for Food Scientists", 1989, Van Nostrand Reinhold ISBN 0-442-20765-4 (Chapter 4—Effect of pH on Activity, Chapter 8Peptide Hydrolases, Chapter 9—Glycoside Hydrolases, Chapter 10—Ester Hydrolases, Chapter 12—Miscellaneous Enzymes).

Accordingly, the present invention provides polypeptides which have been genetically engineered or modified to include a catalytic triad that alters the performance of the polypeptide, and preferably, to include a catalytic triad that alters the pH profile of the polypeptide. In a preferred embodiment, the modified target molecule has an alkaline pH profile as compared to its precursor having an acidic pH profile. Optionally, the modified target molecule is a modified target enzyme, wherein the modified target enzyme is active or stable in a pH range of about 7.0 to about 14.0, and preferably, in a pH range of about 7.0 to about 10.0, in contrast to its precursor having activity or stability at acidic pH below about 6.99. In a particularly preferred embodiment, the genetically modified target enzyme comprises a substitution, deletion or addition of amino acid residue(s) equivalent to one or more of amino acid residues Serine 227, Histidine 200, or Glutamate 139 in the Bacillus cellulase 103 sequence (FIGS. 3A–3E; SEQ ID NO:2). In an even more preferred embodiment, such genetic modification comprises a substitution, deletion or addition of one or more amino acid residues so that the modified target enzyme comprises a catalytic triad containing three amino acid residues equivalent to amino acid residues Serine 227, Histidine 200 and Glutamate 139, respectively, in the Bacillus cellulase 103 sequence (FIGS. 3A–3E, SEQ ID NO:2).

The present invention further provides a nucleic acid molecule comprising DNA encoding an amino acid sequence for the modified target molecules described herein, expression systems incorporating such DNA including vectors and phages, host cells transformed with such DNA, and anti-sense strands of DNA corresponding to the DNA molecule which encodes the amino acid sequence. The present invention includes a method for producing a modified target molecule comprising the step of expressing the DNA incorporated in such an expression system which has been transformed into a host cell. The DNA sequences may be expressed by operably linking them to an expression control sequence in an appropriate expression vector and employing that expression vector to transform an appropriate host according to well known techniques. A wide variety of host/expression vector combinations may be employed in expressing the DNA sequences of this invention. Useful expression vectors, for example, include segments of chromosomal, non-chromosomal and synthetic DNA sequences, such as the various known plasmids and phages useful for this purpose. In addition, any of a wide variety of expression control sequences are generally used in these vectors. Additionally, phage display systems are useful for the invention herein.

A wide variety of host cells are also useful in expressing the DNA sequences of this invention and are contemplated herein. These hosts may include well known eukaryotic and prokaryotic hosts, such as strains of E. coli, Pseudomonas, Bacillus, Streptomyces, various fungi, e.g., Trichoderma or Aspergillus, yeast and animal cells. Preferably, the host expresses the modified target molecule of the present invention extracellularly to facilitate purification and downstream processing. Expression and purification of the modified target molecules of the invention may be effected through art-recognized means for carrying out such processes.

The modified target molecules according to the present invention may exhibit altered performance characteristics providing desirable results which are useful in a variety of applications. For example, modified target enzymes according to the present invention which exhibit altered pH profiles, such as stability and activity at alkaline pH ranges, are useful in detergents and textile industrial compositions, as well as therapeutic or diagnostic applications. Thus, in another embodiment of the present invention there are provided detergent compositions in either liquid, gel or granular form, which comprise modified target molecule(s) according to the present invention. Such detergent compositions will particularly benefit from the addition of modified target molecule(s) according to the present invention which has increased pH profile to improve activity and performance in an industrial setting. The modified target molecules according to the present invention may be advantageously formulated into known powdered, liquid or gel detergents having a pH of between about 7.0 and about 14.0.

Therapeutic and diagnostic compositions comprising the modified target molecules described herein are also provided. The modified target molecules described herein are preferably included in a composition comprising a suitable carrier. Suitable carriers and their formulations are described in Remington's Pharmaceutical Sciences, 16th ed., 1980, Mack Publishing Co., edited by Osol et al. Typically, in such applications, an appropriate amount of a pharmaceutically-acceptable carrier or salt is used in the carrier to render the formulation isotonic. Examples of the carrier include, but are not limited to, saline, Ringer's solution and dextrose solution. The pH of the solution is preferably from about 7.0 to about 10.0 and more preferably from 7.0 to 8.0. It will be apparent to those persons skilled in the art that certain carriers may be more preferable depending upon, for instance, the particular therapeutic or diagnostic use. The carrier may be in the form of a lyophilized formulation or aqueous solution. Acceptable carriers, excipients, or stabilizers are preferably nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN™, PLURONICS™ or polyethylene glycol (PEG). The formulations to be used for in vivo administration or particular diagnostic uses are preferably sterile. This is readily accomplished, e.g., by filtration through sterile filtration membranes.

The following example is offered by way of illustration and not by way of limitation. The disclosures of all patent and literature citations in the specification are expressly incorporated herein by reference.

EXAMPLE

The full length amino acid sequence of Bacillus cellulase 103 (also referred to below as "BCE103") and encoding DNA sequence thereof are provided in FIGS. 3A–3E. The numbering of amino acid residues throughout the present application in reference to cellulase 103 are in accordance with the numbering of the amino acid positions in the sequence provided in FIG. 2.

To analyze the sequence and structure of cellulase 103, an EcoRI-XbaI restriction enzyme fragment from pUCAPR103 [U.S. Pat. No. 6,063,611 issued to Solingen] containing the complete BCE103 coding sequence was ligated into Eco RI-Xba I digested pBS42T vector (a shuttle vector capable of replicating in both E. coli and B. subtilis derived from pBS42 [Band et al., DNA, 3:17–21 (1984)] and containing a strong transcriptional terminator) to generate pBS42T103. BCE103 has two repeated C-terminal cellulose binding domains. A plasmid encoding the BCE103 catalytic core was generated from pBS42T103 by inverse PCR [Dorrell et al., Biotechniques, 21:604, 606, 608 (1996)] using the primers TAAACTATATAATTGATAAAAATTTACTAATGAGA (SEQ ID NO:3) and TGGCGGAATAGATGCTGAT-TCTCTTATTTTTTCCC (SEQ ID NO:4) to generate the plasmid pCORE3. The protein sequence encoded by pCORE3 is

DDYSVVEEHGQLSISNGELVNERGEQVQLKGMSSHGLQWYGQFVNYESMKWLRDDWGITVFRAA (SEQ ID NO:5)

MYTSSGGYIDDPSVKEKVKETVEAAIDLGIYVIIDWHILSDNDPNIYKEEAKDFFDEMSELYGD

YPNVIYEIANEPNGSDVTWDNQIKPYAEEVIPVIRDNDPNNIVIVGTGTWSQDVHHAADNQLAD

PNVMYAFHFYAGTHGQNLRDQVDYALDQGAAIFVSEWGTSAATGDGGVFLDEAQVWIDFMDERN

LSWANWSLTHKDESSAALMPGANPTGGWTEAELSPSGTFVREKIRESASIPP.

pCORE3 was transformed into Bacillus subtilis BG3934 [Naki et al., *Applied Microbiology and Biotechnology*, 49:290–294 (1998)]. BG3934 has been deleted in several proteases: ?aprE, ?nprE, ?epr, ?isp, ?bpf. The strains were grown in shake flasks essentially as described by Naki et al., *supra*. The secreted BCE103 catalytic core sequence was then recovered from Bacillus subtilis cultures as follows. The supernatant was adjusted to pH 8.0 with 1M Tris:HCl and diafiltered with 50 mM Tris:HCl pH 8.0 until the ionic strength was less than or equal to that of 75 mM Tris:HCl pH 8.0. Ion exchange chromatography was carried out using BioSepra 20 μM HyperD DEAE resin equilibrated in 50 mM Tris:HCl pH 8.0 and developed with a NaCl gradient in the same buffer. The fractions containing activity were combined, adjusted to 1M with ammonium sulfate and applied to a Poros PH2 hydrophobic affinity column developed with a 1–0M ammonium sulfate gradient in 50 mM Tris:HCl pH 8.0, and the fractions containing activity were again combined. The material was concentrated and exchanged into 50 mM Tris:HCl pH 8.0 using standard techniques.

The catalytic core sequence of cellulase 103 crystallized in 0.5–1.0M ammonium sulfate in 200 mM sodium cacodylate pH 5.5–7.0. The space group is no. 19, with cell dimensions a=60.44 Å, b=78.16 Å, c=55.05 Å, with 1 molecule/asymmetric unit. Reflections were recorded with a R-axis II image plate (Molecular Structures Corp.), utilizing CuKα radiation from an RU200B rotating anode (Rigaku Corp.), and reduced to structure factor amplitudes using programs distributed with the data collection system. Data were scaled together, and difference Patterson and difference Fourier maps were calculated using XtalView [McRee, *J. Struct. Biol.*, 125:156–165 (1999)]. The heavy atom positions of 5 derivatives were determined by inspection of difference Patterson maps, and placed in a common coordinate frame using derivative anomalous scattering. Subsequent maximum likelihood heavy-atom refinement and phasing was performed with SHARP [LaFortelle et al., *Methods in Enzymology*, 276:472–493 (1997)], and the resultant phases improved further by solvent flipping in SOLOMON. The resultant electron density maps were of excellent quality, and an unambiguous chain trace was obtained with Xautofit (Molecular Simulations Inc.). Subsequently, the model was built with Xfit (McRee, supra} and refined using Xplor3.1 [Brunger, *X-plor Version 3.1 A system for X-ray crystallography and NMR*, Yale University Press, New Haven Conn., 1992]. Water molecules were added using Xsolvate (Molecular Simulations Inc.).

The data from the analysis is shown in Tables 1 and 2 below, and includes comparisons to other GH-5 family enzymes. The non-bonded contact distances of the catalytic triad of the GH-5 enzymes are shown. In Table 2, reference is made to the following molecules: BCE103; cellulase 103. 4A3H; *Bacillus agaradherans* Cel5A [Davies et al., *Biochemistry*, 37:11707–11713 (1998)]. 1EGZ; *Erwinia crysanthemi* cel5A (unpublished). 1QNQ; *Hypochrea jecorina* β-mannase [Sabini et al., *Acta Crystall. D. Biol. Crystall.*, 56:3–13 (2000)]. 1CZE; *Candida albicans* exo-1,3-glucanase [Cutfield et al., *supra*]. 1BQC; *Thermobifida flisca* β-mannase [Hilge et al., *Structure*, 6:1433–1444 (1998)]. 1C0D; *Acidothermus cellulyticus* endo-1,4-glucanase [Sakon et al., supra]. 1EDG; *Clostridium cellulolytcum* endo-1,4 glucanase A [Ducros et al., *Structure*, 3:939–949 (1995)]. Distance 1 is the separation between the OE2 of the glutamate, and ND1 of the histidine. Distance 2 is the separation between NE2 of the histidine and the proton donor of the third group, the identity of which is given in the next column, and the type of triad (discussed below) each corresponds to is given in the final column.

The acid/base catalyst in cellulase 103 was postulated to be glutamate 139 and the nucleophile to be glutamate 228. The two carboxylate groups are approximately 5.0 Å apart, which is consistent with an enzyme hydrolysing the beta-1, 4-glycosidic bond via a double displacement mechanism, with a glucosyl enzyme intermediate, which retains the anomeric configuration in the product [White et al., *Curr. Op. Struct. Biol.*, 7:645 (1997)]. Adjacent to glutamate 139 is histidine 200, between which there is a short 2.63 Å hydrogen bond, between atoms OE2 and ND1. Also in close proximity to histidine 200 is serine 227, with a hydrogen bond between NE2 and OG of 2.77 Å. These three hydrogen-bonded residues, glutamate 139, histidine 200, and serine 227, were identified by Applicants as a functioning catalytic triad in cellulase 103. The catalytic triad has certain similarities to the triad previously observed by Schrag et al., *Nature*, 351:761–764 (1991) in a lipase molecule.

TABLE 1

| | Methods, data collection, and refinement statistics | | | | | |
|---|---|---|---|---|---|---|
| | Native | PTCL[1] | PTCN[2] | UOAC[3] | MPBAC[4] | HGI[5] |
| Data collection Statistics | | | | | | |
| Resolution. | 1.7 | 2.0 | 2.0 | 2.2 | 2.0 | 2.0 |
| Observed refs. | 139842 | 118339 | 119332 | 87350 | 90299 | 95939 |
| Unique refs. | 32428 | 20334 | 20330 | 15679 | 19195 | 16965 |
| Complete (%) | 97.7 | 96.8 | 98.6 | 96.6 | 85.4 | 62.1 |

TABLE 1-continued

Methods, data collection, and refinement statistics

|  | Native | PTCL[1] | PTCN[2] | UOAC[3] | MPBAC[4] | HGI[5] |
|---|---|---|---|---|---|---|
| Rsym | 7.7 | 8.5 | 7.7 | 10.6 | 10.2 | 6.57 |
| Rderiv. | — | 0.23 | 0.37 | 0.17 | 0.20 | 0.18 |
| Phasing statistics |  |  |  |  |  |  |
| No. sites. | — | 1 | 1 | 2 | 4 | 4 |
| Reullis | — | 0.70 | 0.67 | 0.65 | 0.65 | 0.58 |
| Phasing power | — | 1.41 | 1.13 | 1.48 | 1.32 | 1.70 |
| Refinement Statistics |  |  |  |  |  |  |
| R-factor | 0.22 |  |  |  |  |  |
| Bonds (Å) | 0.014 |  |  |  |  |  |
| Angles (°) | 1.79 |  |  |  |  |  |
| Dihedrals (°) | 28.46 |  |  |  |  |  |
| Impropers (°) | 1.58 |  |  |  |  |  |

[1]Platinum tetrachloride.
[2]Platinum tetracyanide.
[3]Uranyl acetate.
[4]Trimethy lead acetate.
[5]Mercury triiodide.

TABLE 2

| PDB Code | Distance 1 (Å) | Distance 2 (Å) | Third ligand (atom) | Triad Type |
|---|---|---|---|---|
| BCE103 | 2.63 | 2.77 | Serine (OG) | A |
| 4A3H | 2.59 | 2.72 | Serine (OG) | A |
| 1EGZ | 2.84 | 2.74 | Threonine (OG1) | A |
| 1QNQ | 2.67 | 2.86 | Glutamate (OE2) | B |
| 1CZ1 | 2.57 | 2.74 | Asparagine (OD2) | B |
| 1BQC | 2.61 | 2.82 | Water (O) | C |
| 1C0D | 2.73 | 2.82 | Water (O) | C |
| 1EDG | 2.82 | 2.73 | Water (O) | C |

Cellulase 103 belongs to GH5 sub-family 2 (GH5-2) [Wang et al., *J. Biol. Chem.*, 268:14096–14102 (1993); Beguin, *Ann. Rev. Microbiol.*, 44:219–248 (1990)]. In the analysis of this sub-family, serine and threonine residues were consistently observed at the equivalent position of serine 227. The structure of the GH5-2 *Erwinia chrysanthemi* cel5A showed that threonine at this position also forms a catalytic triad (PDB code 1EGZ). In one sequence of the GH5-3 enzymes, that from Fibrobacter succinogenes [McGavin et al., *J. Bacteriol.*, 171:5587–5595 (1989)], an asparagine residue was found at the equivalent of serine 227. Such catalytic triads have been referred to by Applicants as type A ("CT-A"). The serine/threonine/asparagine is immediately N-terminal to the nucleophile glutamate 228, and thus the presence of those residues at that position was identified as being characteristic of CT-A.

In two other GH5 structures, it was found that instead of the equivalent of serine/threonine 227, the third member of the triad can alternatively be an asparagine or aspartate residue from β-strand(s) adjacent to serine 227. The side-chain of aspartate 251 of the *Candida albicans* exo-1,3-glucanase [Cutfield et al., *J. Mol. Biol.*, 294:771–783 (1999)] includes a potential hydrogen bond donor in a structurally conserved position to the hydroxyl oxygen of serine 227. In the *Clostridium thermocellum* cel5 [Dominguez et al., *J. Mol. Biol.*, 257:1042–1051 (1996)], asparagine 196 is equivalent to this aspartate. In the crystal structures, the hydrogen-bonding pattern of the triad is not observed, but in this enzyme, there appears to be induced fit by the substrate, which may account for the discrepancy. In these types of enzymes, there is an Asx/His/Glu triad, which as described herein, is referred to by Applicants as catalytic triad type B ("CT-B"). The aspartate/asparagine is found two residues N-terminal to the strictly conserved histidine 200 and thus its presence is found to be characteristic of CT-B. This type of triad appears to be found in GH5-3, with the exception of the F. succinogenes GH5 enzyme discussed above.

The sequences of most other GH5 enzymes revealed that they have neither a CT-A nor a CT-B structure. Analysis of the known structures [Ducros et al., *Structure*, 3:939–949 (1995); Sakon et al., *Biochemistry*, 35:10648–10660 (1996); Hilge et al., *Structure*, 6:1433–14444 (1998)] of three such enzymes reveal that they have a water molecule positioned in approximately the same position as the proton donor observed in CT-A and CT-B. Such a catalytic triad consists of a water/His/Glu triad, and as described herein, such a triad is referred to by Applicants as type C ("CT-C"). From the sequence alignment reported in Wang et al., supra, it appears that all GH5-1 and GH5-4 enzymes include a CT-C. Interestingly, the Robillarda Cel5 [Yoshigi et al., *J. Biochem. (Tokyo)*, 108:388–392 (1990)], and Trichoderma EG2 GH5-5 enzymes appear to have potential hydrogen bond donors for both a CT-A and CT-B.

There is a short 2.6 Å hydrogen-bond distance between the histidine and asparate residues of certain classic triads [Kuhn et al., *Biochemistry*, 37:13446–13452 (1998)]. A 2.6 Å A hydrogen bond distance is similarly observed between the histidine and glutamate of the GH5 triads (see Table 2 above), suggesting that these triads are functional. In the serine protease-like enzymes, the catalytic triad functions as a 'charge relay system' [Blow et al., *Nature*, 221:337–340 (1969)]. This makes the serine a potent nucleophile, which can attack the peptide bond. However, in cellulase 103, the serine is not required to act as such. Indeed, it is buried in the interior of the protein, as are the hydrogen bond donors to the histidine in all of the observed triads in GH5. In GH5 enzymes, a glutamate is the nucleophile [Wang et al., *supra*].

For an active GH5 enzyme, the proton donor glutamate must be protonated, and the nucleophilic glutamate unprotonated, i.e their pKas must be differentiated. There is evidence from studies of GH11 enzymes that the close proximity of the glutamates (~5.5 Å) in the retaining GHs may assist in this function. McIntosh et al. *Biochemistry*, 35:9958–9966 (1996), measured directly the pKa of the catalytic groups of the GH-11 xylanase from *B. circulans*. The pKa of the nucleophile was 4.6 and therefore not greatly attenuated. The pKa of the proton donor was 6.7, and therefore shifted significantly up. Mutagenesis of the nucleophile to a glutamine resulted in a lowering of the pKa of the proton donor to 4.2. Thus, the pKas of the two glutamates appear to be coupled.

It has been proposed that in the charge relay mechanism [Blow et al., *supra*], the histidine residue protonates the aspartate residue, despite the pKa differences of these sidechain types in solution. Serine in turn is proposed to protonate the histidine, making the serine a more potent nucleophile. A similar effect would shift the pKa of glutamate 139 of cellulase 103, ensuring that it is protonated, not the glutamate 238 nucleophile. However, the deprotonation of serine is induced by substrate-binding. In GH5 enzymes where the proton donor is water, or aspartate, the hydrogen bond donor may indeed deprotonate. However, it is believed that the serine, threonine and asparagine of CT-A are unlikely to do so. The structure of the cellulase 103 shows that it also has a short ~2.6 Å hydrogen bond from the side-chain hydroxyl group to the carboxyl group of glutamate 135. Glutamate 135 is strongly conserved in GH5-2, GH5-3, GH5-4, and completely shielded from bulk solvent. Such internally sequestered carboxylate groups are often protonated because of a considerably increased pKa, due to the low internal dielectric constant. If serine or threonine protonate the histidine, it is likely that they will immediately deprotonate glutamate 135. The overall effect will be to raise the pKa of the solvent exposed proton donor glutamate, by coupling it to an internally sequestered glutamate via a charge relay mechanism. In GH5-1, aspartate is found at the equivalent of glutamate 135 and the known structures have a rather long hydrogen bond distance (~3.1 Å) to the water of CT-C. It is possible that the proton donor glutamate is also coupled to an internally sequestered carboxylate in such enzymes. In the two GH5-5 sequences analyzed having a CT-A and CT-B discussed above, no equivalent to glutamate 135 was present. However, at the proton donor site for CT-B, the enzymes have a glutamate residue, and this residue may play an equivalent role to glutamate 135. The pH optima of the GH5 enzymes varies from acidic to alkaline. As the histidine and glutamate members of the catalytic triad are strictly conserved, it is likely that the nature of the proton donor to histidine will attenuate the shift in the pKa of the proton donor glutamate. For example, at high pH, water will probably deprotonate, and thus be unable to donate a hydrogen bond to the histidine. Serine and threonine will not deprotonate, and therefore GH-2 enzymes would be expected to continue to be active in alkaline conditions [Park et al., *Protein Eng.*, 6:921–926 (1993)].

SEQUENCE LISTING

<160> NUMBER OF SEQ ID NOS: 5

<210> SEQ ID NO 1
<211> LENGTH: 1404
<212> TYPE: DNA
<213> ORGANISM: Bacillus sp.

<400> SEQUENCE: 1

```
atgaaaaaga taactactat ttttgccgta ttgctcatga cattggcgtt gttcagtata      60
ggaaacacga cagcggctga tgattattca gttgtagagg aacatgggca actaagtatt     120
agtaacggtg aattagtcaa tgaacgaggc gaacaagttc agttaaaagg gatgagttcc     180
catggtttgc aatggtacgg tcaatttgta aactatgaaa gcatgaaatg gctaagagat     240
gattggggaa taactgtatt ccgagcagca atgtatacct cttcaggagg atatattgac     300
gatccatcag taaaggaaaa agtaaaagag actgttgagg ctgcgataga ccttggcata     360
tatgtgatca ttgattggca tatcctttca gacaatgacc cgaatatata taagaagaa      420 gcgaaggatt tctttgatga atgtcagag ttgtatggag actatccgaa tgtgatatac      480
gaaattgcaa atgaaccgaa tggtagtgat gttacgtggg acaatcaaat aaaaccgtat     540
gcagaagaag tgattccggt tattcgtgac aatgacccta ataacattgt tattgtaggt     600
acaggtacat ggagtcagga tgtccatcat gcagccgata atcagcttgc agatcctaac     660
gtcatgtatg catttcattt ttatgcagga acacatggac aaaatttacg agaccaagta     720
gattatgcat tagatcaagg agcagcgata tttgttagtg aatggggggac aagtgcagct     780 acaggtgatg gtggtgtgtt tttagatgaa gcacaagtgt ggattgactt tatggatgaa     840
```

```
agaaatttaa gctgggccaa ctggtctcta acgcataagg atgagtcatc tgcagcgtta    900
atgccaggtg caaatccaac tggtggttgg acagaggctg aactatctcc atctggtaca    960
tttgtgaggg aaaaaataag agaatcagca tctattccgc caagcgatcc aacaccgcca   1020
tctgatccag gagaaccgga tccaggagaa ccggatccaa cgcccccaag tgatccagga   1080
gagtatccag catgggattc aaatcaaatt tacacaaatg aaattgtgta tcataacggt   1140
cagttatggc aagcgaaatg gtggacacaa aatcaagagc aggtgaccc atacggtccg   1200 tgggaaccac tcaaatctga cccagattca ggagaaccgg atccaacgcc cccaagtgat   1260
ccaggagagt atccagcatg ggattcaaat caaatttaca caaatgaaat tgtgtaccat   1320
aacggccagc tatggcaagc aaaatggtgg acacaaaatc aagagccagg tgacccatat   1380
ggtccgtggg aaccactcaa ttaa                                          1404
```

<210> SEQ ID NO 2
<211> LENGTH: 467
<212> TYPE: PRT
<213> ORGANISM: Bacillus sp.

<400> SEQUENCE: 2

```
Met Lys Lys Ile Thr Thr Ile Phe Ala Val Leu Leu Met Thr Leu Ala
  1               5                  10                  15

Leu Phe Ser Ile Gly Asn Thr Thr Ala Ala Asp Asp Tyr Ser Val Val
                 20                  25                  30

Glu Glu His Gly Gln Leu Ser Ile Ser Asn Gly Glu Leu Val Asn Glu
             35                  40                  45

Arg Gly Glu Gln Val Gln Leu Lys Gly Met Ser Ser His Gly Leu Gln
 50                  55                  60

Trp Tyr Gly Gln Phe Val Asn Tyr Glu Ser Met Lys Trp Leu Arg Asp
 65                  70                  75                  80

Asp Trp Gly Ile Thr Val Phe Arg Ala Ala Met Tyr Thr Ser Ser Gly
                 85                  90                  95

Gly Tyr Ile Asp Asp Pro Ser Val Lys Glu Lys Val Lys Glu Thr Val
            100                 105                 110

Glu Ala Ala Ile Asp Leu Gly Ile Tyr Val Ile Ile Asp Trp His Ile
            115                 120                 125

Leu Ser Asp Asn Asp Pro Asn Ile Tyr Lys Glu Glu Ala Lys Asp Phe
130                 135                 140

Phe Asp Glu Met Ser Glu Leu Tyr Gly Asp Tyr Pro Asn Val Ile Tyr
145                 150                 155                 160

Glu Ile Ala Asn Glu Pro Asn Gly Ser Asp Val Thr Trp Asp Asn Gln
                165                 170                 175

Ile Lys Pro Tyr Ala Glu Glu Val Ile Pro Val Ile Arg Asp Asn Asp
            180                 185                 190

Pro Asn Asn Ile Val Ile Val Gly Thr Gly Thr Trp Ser Gln Asp Val
            195                 200                 205

His His Ala Ala Asp Asn Gln Leu Ala Asp Pro Asn Val Met Tyr Ala
        210                 215                 220

Phe His Phe Tyr Ala Gly Thr His Gly Gln Asn Leu Arg Asp Gln Val
225                 230                 235                 240

Asp Tyr Ala Leu Asp Gln Gly Ala Ala Ile Phe Val Ser Glu Trp Gly
                245                 250                 255

Thr Ser Ala Ala Thr Gly Asp Gly Gly Val Phe Leu Asp Glu Ala Gln
            260                 265                 270
```

```
Val Trp Ile Asp Phe Met Asp Glu Arg Asn Leu Ser Trp Ala Asn Trp
        275                 280                 285

Ser Leu Thr His Lys Asp Glu Ser Ser Ala Ala Leu Met Pro Gly Ala
        290                 295                 300

Asn Pro Thr Gly Gly Trp Thr Glu Ala Glu Leu Ser Pro Ser Gly Thr
305                 310                 315                 320

Phe Val Arg Glu Lys Ile Arg Glu Ser Ala Ser Ile Pro Pro Ser Asp
                325                 330                 335

Pro Thr Pro Pro Ser Asp Pro Gly Glu Pro Asp Pro Gly Glu Pro Asp
                340                 345                 350

Pro Thr Pro Pro Ser Asp Pro Gly Glu Tyr Pro Ala Trp Asp Ser Asn
                355                 360                 365

Gln Ile Tyr Thr Asn Glu Ile Val Tyr His Asn Gly Gln Leu Trp Gln
        370                 375                 380

Ala Lys Trp Trp Thr Gln Asn Gln Glu Pro Gly Asp Pro Tyr Gly Pro
385                 390                 395                 400

Trp Glu Pro Leu Lys Ser Asp Pro Asp Ser Gly Pro Asp Pro Asp Thr
                405                 410                 415

Pro Pro Ser Asp Pro Gly Glu Tyr Pro Ala Trp Asp Ser Asn Gln Ile
                420                 425                 430

Tyr Thr Asn Glu Ile Val Tyr His Asn Gly Gln Leu Trp Gln Ala Lys
                435                 440                 445

Trp Trp Thr Gln Asn Gln Glu Pro Gly Asp Pro Tyr Gly Pro Trp Glu
        450                 455                 460

Pro Leu Asn
465

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
taaactatat aattgataaa aatttactaa tgaga                    35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
tggcggaata gatgctgatt ctcttatttt ttccc                   35

<210> SEQ ID NO 5
<211> LENGTH: 308
<212> TYPE: PRT
<213> ORGANISM: Artificial Sequence
<220> FEATURE:
<223> OTHER INFORMATION: protein encoded by plasmid pCORE3

<400> SEQUENCE: 5

Asp Asp Tyr Ser Val Val Glu Glu His Gly Gln Leu Ser Ile Ser Asn
 1               5                  10                  15

Gly Glu Leu Val Asn Glu Arg Gly Glu Gln Val Gln Leu Lys Gly Met
            20                  25                  30
```

```
Ser Ser His Gly Leu Gln Trp Tyr Gly Gln Phe Val Asn Tyr Glu Ser
        35              40              45
Met Lys Trp Leu Arg Asp Asp Trp Gly Ile Thr Val Phe Arg Ala Ala
    50              55              60
Met Tyr Thr Ser Ser Gly Gly Tyr Ile Asp Asp Pro Ser Val Lys Glu
65              70              75              80
Lys Val Lys Glu Thr Val Glu Ala Ala Ile Asp Leu Gly Ile Tyr Val
            85              90              95
Ile Ile Asp Trp His Ile Leu Ser Asp Asn Asp Pro Asn Ile Tyr Lys
            100             105             110
Glu Glu Ala Lys Asp Phe Phe Asp Glu Met Ser Glu Leu Tyr Gly Asp
            115             120             125
Tyr Pro Asn Val Ile Tyr Glu Ile Ala Asn Glu Pro Asn Gly Ser Asp
    130             135             140
Val Thr Trp Asp Asn Gln Ile Lys Pro Tyr Ala Glu Glu Val Ile Pro
145             150             155             160
Val Ile Arg Asp Asn Asp Pro Asn Asn Ile Val Ile Val Gly Thr Gly
            165             170             175
Thr Trp Ser Gln Asp Val His His Ala Ala Asp Asn Gln Leu Ala Asp
            180             185             190
Pro Asn Val Met Tyr Ala Phe His Phe Tyr Ala Gly Thr His Gly Gln
            195             200             205
Asn Leu Arg Asp Gln Val Asp Tyr Ala Leu Asp Gln Gly Ala Ala Ile
    210             215             220
Phe Val Ser Glu Trp Gly Thr Ser Ala Ala Thr Gly Asp Gly Gly Val
225             230             235             240
Phe Leu Asp Glu Ala Gln Val Trp Ile Asp Phe Met Asp Glu Arg Asn
            245             250             255
Leu Ser Trp Ala Asn Trp Ser Leu Thr His Lys Asp Glu Ser Ser Ala
            260             265             270
Ala Leu Met Pro Gly Ala Asn Pro Thr Gly Gly Trp Thr Glu Ala Glu
    275             280             285
Leu Ser Pro Ser Gly Thr Phe Val Arg Glu Lys Ile Arg Glu Ser Ala
    290             295             300
Ser Ile Pro Pro
305
```

The invention claimed is:

1. An isolated, modified target enzyme of SEQ ID NO:2, comprising a polypeptide genetically modified to comprise a catalytic triad that alters the pH profile of the polypeptide, wherein said catalytic triad comprises a first member, a second member and a third member and said first member is a proton donor, said second member is the Histidine 200 residue in the Bacillus cellulase 103 sequence (SEQ ID NO:2), and said third member is the Serine 227 residue in the Bacillus cellulase 103 sequence (SEQ ID NO:2).

2. The modified target enzyme of claim 1 wherein said pH profile is an alkaline pH profile.

3. The modified target enzyme of claim 1 wherein the genetic modification in the polypeptide comprises a substitution, deletion or addition of amino acid residue(s) wherein said amino acid residues are selected from the group consisting of Serine 227, Histidine 200, and Glutamate 139 in the Bacillus cellulase 103 sequence (SEQ ID NO:2).

4. The modified target enzyme of claim 1 wherein said enzyme is a cellulase.

5. The modified target enzyme of claim 1 wherein said enzyme is a hydrolase.

6. A modified target enzyme, the modified target enzyme being modified from SEQ ID NO:2, the modified enzyme being produced according to the following method of producing a modified target enzyme having an altered performance profile, comprising the steps of:

(a) providing a target enzyme;

(b) analyzing said target enzyme to identity one or more regions or amino acid residues in the target enzyme for modification;

(a) modifying said one or more regions or amino acid residues identified in the target enzyme so as to introduce a catalytic triad in the target enzyme, wherein said catalytic triad includes a first member comprising an amino acid residue or chemical group which acts as a proton donor, a second member which is histidine 200 in the sequence of Bacillus cellulase 103 (SEQ ID NO:2), and a third member which is serine 227 in the sequence of Bacillus cellulase 103 (SEQ ID NO:2); and (d) selecting a modified target enzyme having an altered performance profile as compared to the target enzyme of (a).

* * * * *